United States Patent
Arbibe et al.

(10) Patent No.: US 8,092,989 B2
(45) Date of Patent: Jan. 10, 2012

(54) TARGETING THE HISTONE CODE AS A BACTERIAL STRATEGY FOR SELECTIVELY MODULATING GENE EXPRESSION

(75) Inventors: Laurence Arbibe, Paris (FR); Philippe Sansonetti, Paris (FR); Claude Parsot, Paris (FR); Kim Dong Wook, Seoul (KR); Armelle Phalipon, Paris (FR)

(73) Assignees: Institut Pasteur, Paris (FR); Inserm (Institut National de la Sante et de la Recherche Medicale), Paris (FR)

( * ) Notice: Subject to any disclaimer, the term of this patent is extended or adjusted under 35 U.S.C. 154(b) by 176 days.

(21) Appl. No.: 11/992,155

(22) PCT Filed: Sep. 15, 2006

(86) PCT No.: PCT/EP2006/066406
§ 371 (c)(1),
(2), (4) Date: Sep. 9, 2009

(87) PCT Pub. No.: WO2007/031574
PCT Pub. Date: Mar. 22, 2007

(65) Prior Publication Data
US 2009/0324646 A1    Dec. 31, 2009

Related U.S. Application Data

(60) Provisional application No. 60/716,931, filed on Sep. 15, 2005.

(51) Int. Cl.
*C12Q 1/00* (2006.01)
*C12N 5/00* (2006.01)
*C12N 5/071* (2006.01)
*A61K 39/00* (2006.01)
*A61K 39/38* (2006.01)
*A61K 39/02* (2006.01)

(52) U.S. Cl. ...... 435/4; 424/184.1; 424/234.1; 435/325; 435/366; 435/367; 435/372

(58) Field of Classification Search .................. None
See application file for complete search history.

(56) References Cited

U.S. PATENT DOCUMENTS 5,807,685 A * 9/1998 Flavell et al. .................. 435/7.1

OTHER PUBLICATIONS

Jobin et al. (The Journal of Immunology, 1999, 163:3474-3483).*
Buchrieser et al.; "The Virulence Plasmid PWR100 and the Repertoire of Proteins Secreted by the Type III Secretion Apparatus of *Shigella flexneri*", Molecular Microbiology, vol. 38, No. 4, pp. 760-771, (2000).
Buchrieser et al.; "The Virulence Plasmid PWR100 and the Repertoire of Proteins Secreted by the Type III Secretion Apparatus of *Shigella flexneri*", Database Protein [Online] NCBI, Abstract of Molecular Microbiology, vol. 38, No. 4, pp. 760-771, (2000).
Torres; "Current Aspects of *Shigella pathogenesis*", Revista Latinoamericana de Microbiologia, ALAM, vol. 46, Nos. 3-4, pp. 89-97, (2004).
Akins-et al.; "Evidence for in Vivo But Not in Vitro Expression of a *Borrelia burgdorferi* Outer Surface Protein F (OSPF) Homologue", Molecular Microbiology, vol. 18, No. 3, pp. 507-520, (1995).
Arbibe et al.; "An Injected Bacterial Effector Targets Chromatin Access for Transcription Factor NF-$\kappa$B to Alter Transcription of Host Genes Involved in Immune Responses", Nature Immunology, vol. 8, No. 1, pp. 47-56, (2007).

* cited by examiner

*Primary Examiner* — Oluwatosin Ogunbiyi
(74) *Attorney, Agent, or Firm* — Finnegan, Henderson, Farabow, Garrett & Dunner, LLP

(57) ABSTRACT

The ospF gene of *Shigella flexneri* encodes a phosphatase, which is a member of a new class of phosphatases. The OspF phosphatase inhibits the activity of several proteins either by direct protein modification or transcription downregulation. These proteins include MAP kinase, IL-8, CCL20, IL-12, AP1, CREB, RPA p32, and BCL2 related proteins. Methods for treating diseases using OspF phosphatase, methods for identifying agents that modulate OspF phosphatase's activity, methods for identifying agents that mimic OspF phosphatase's activity, and immunogenic compositions comprising OspF phosphatase are provided. A strain of *Shigella flexneri* containing an inactivated ospF gene is also provided.

15 Claims, 26 Drawing Sheets
(10 of 26 Drawing Sheet(s) Filed in Color)

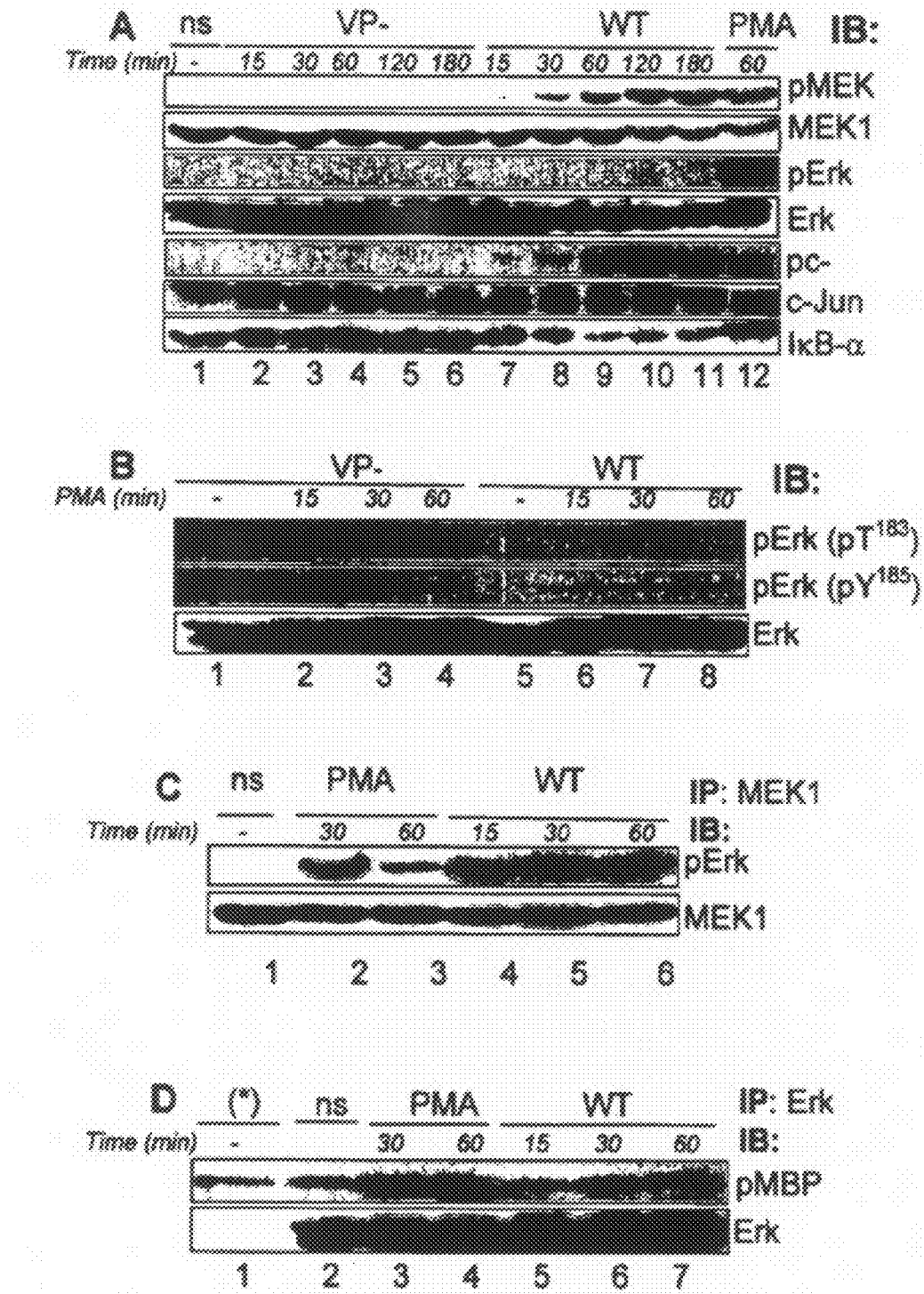

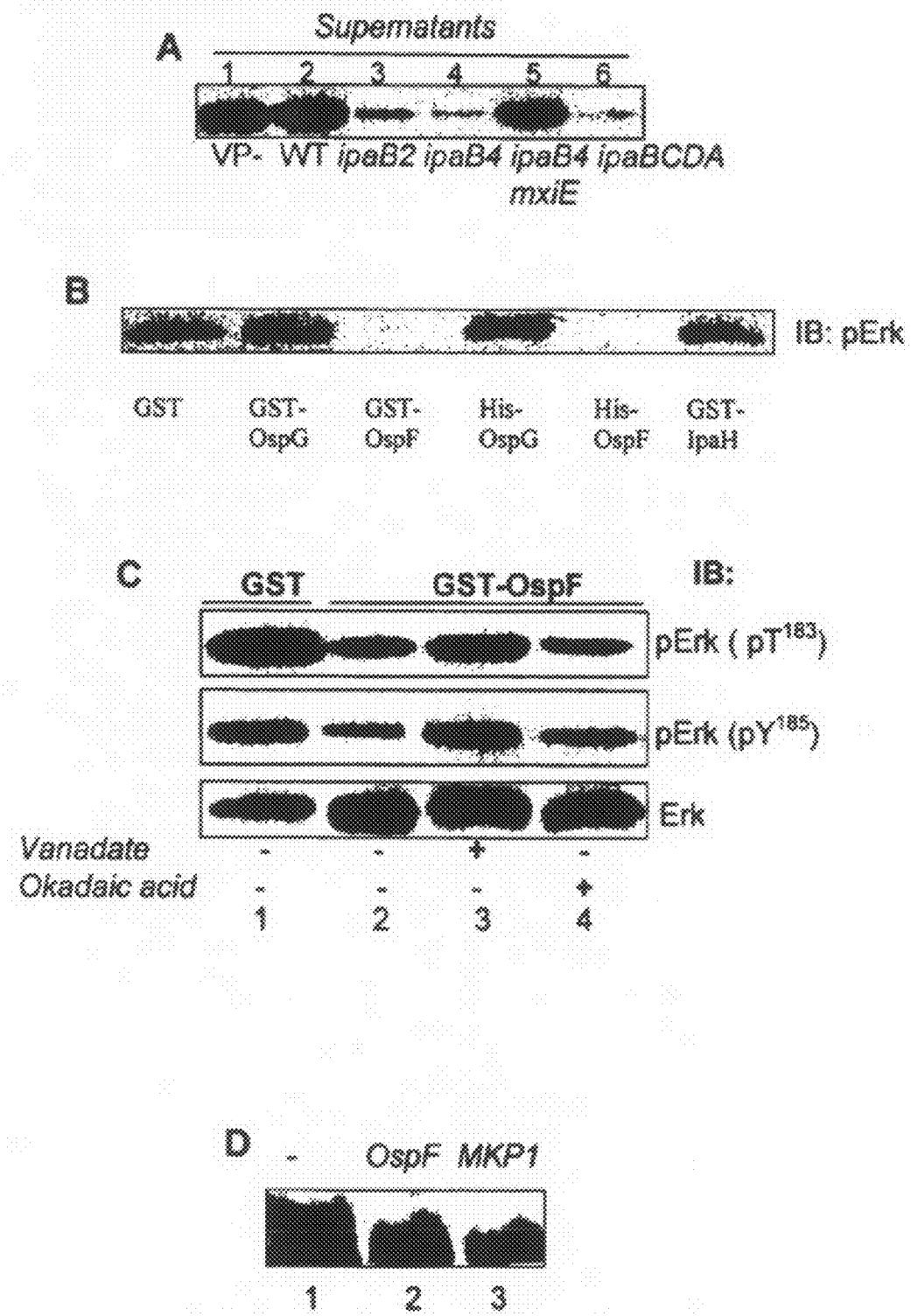

FIGURE 2 CONTINUED
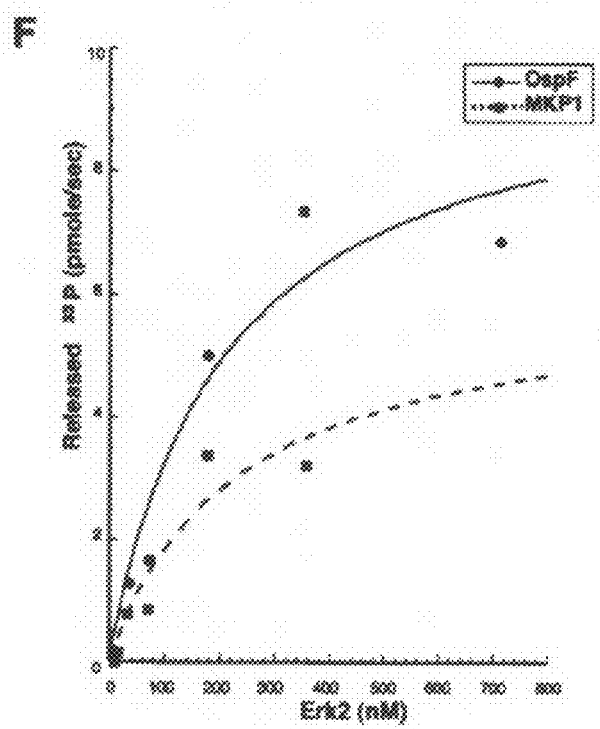
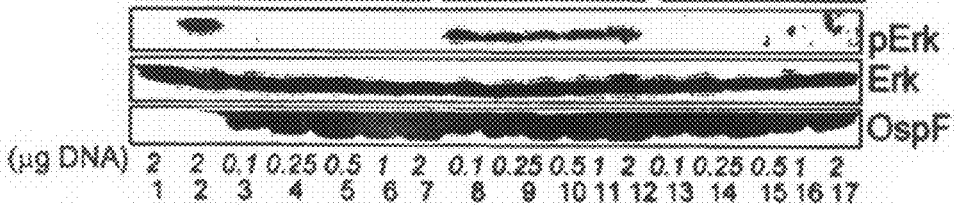

FIGURE 2 CONTINUED
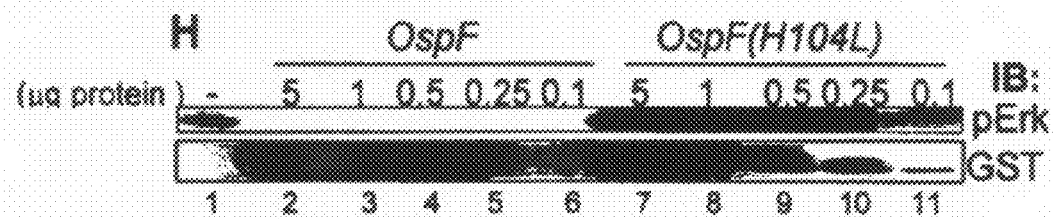
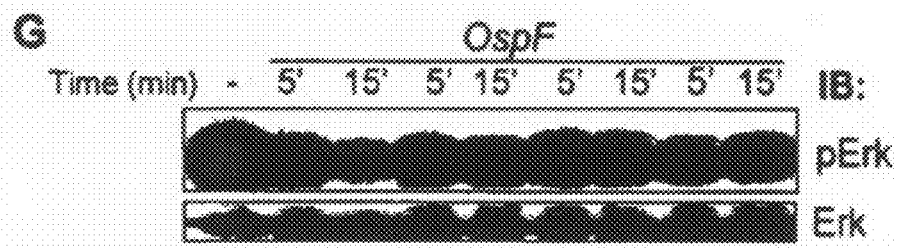

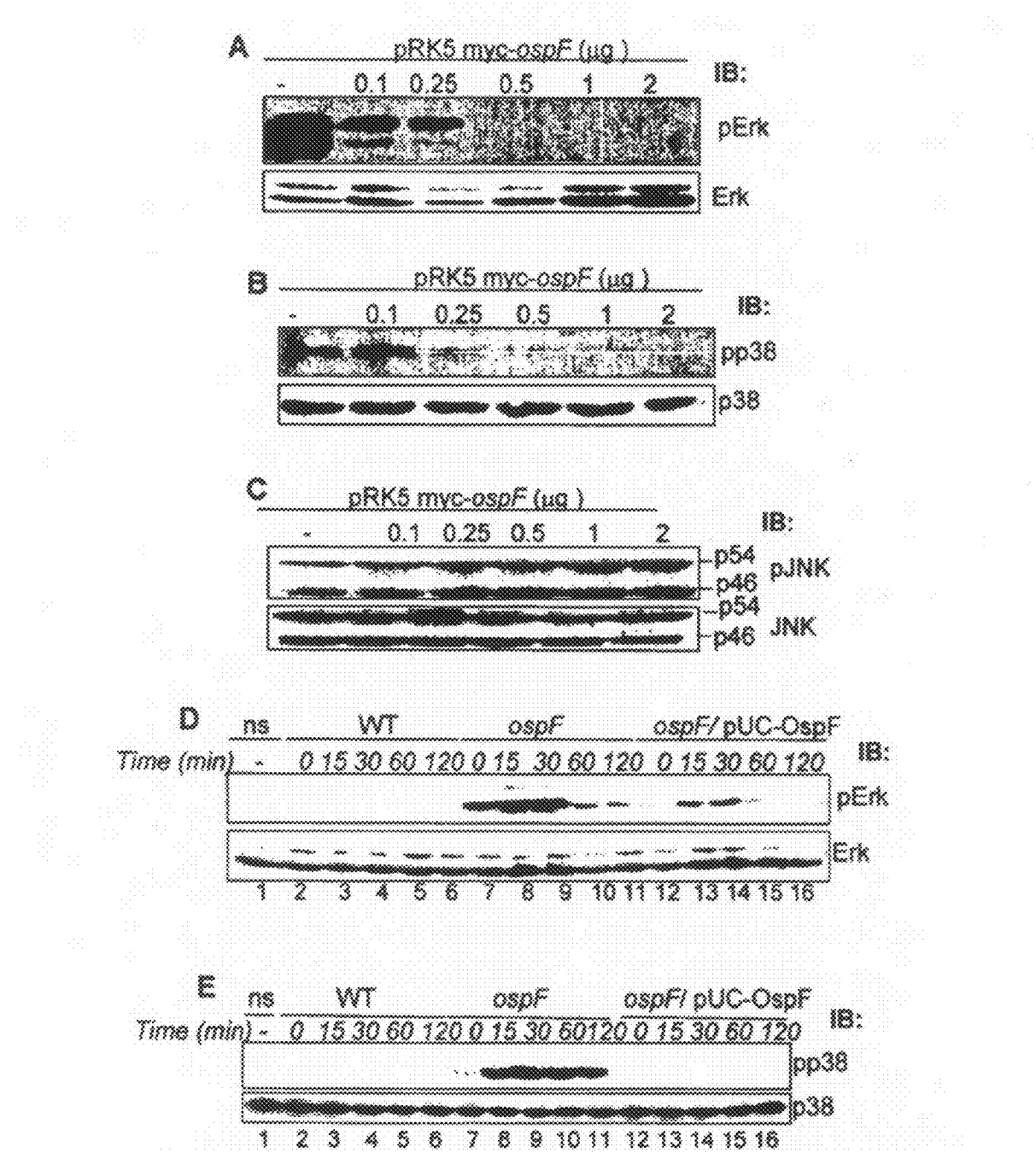

FIGURE 3 CONTINUED
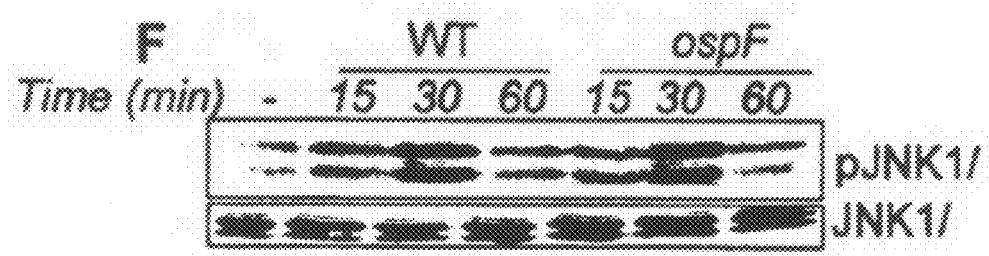
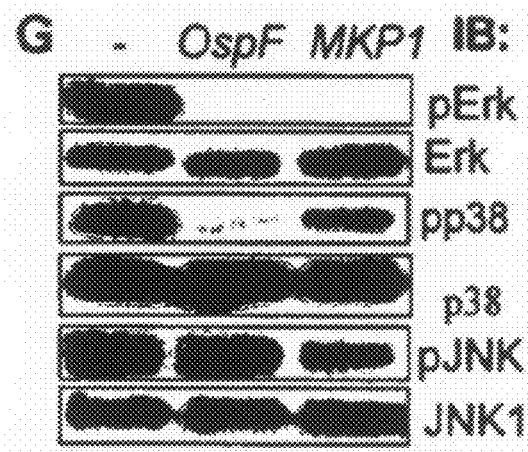

FIGURE 3 CONTINUED
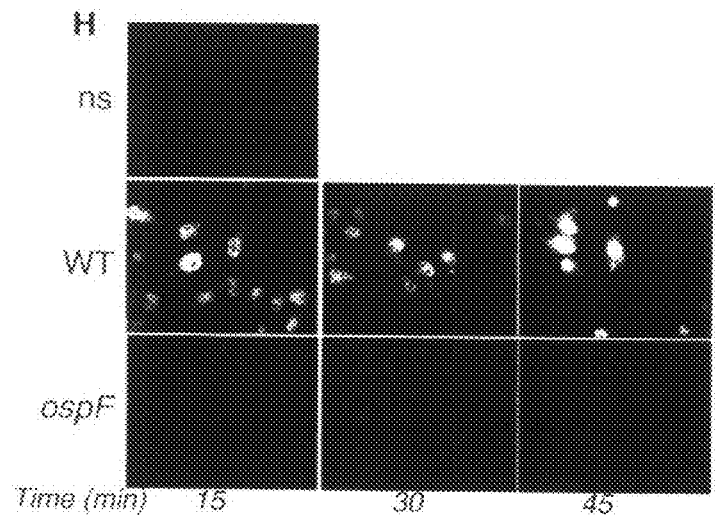
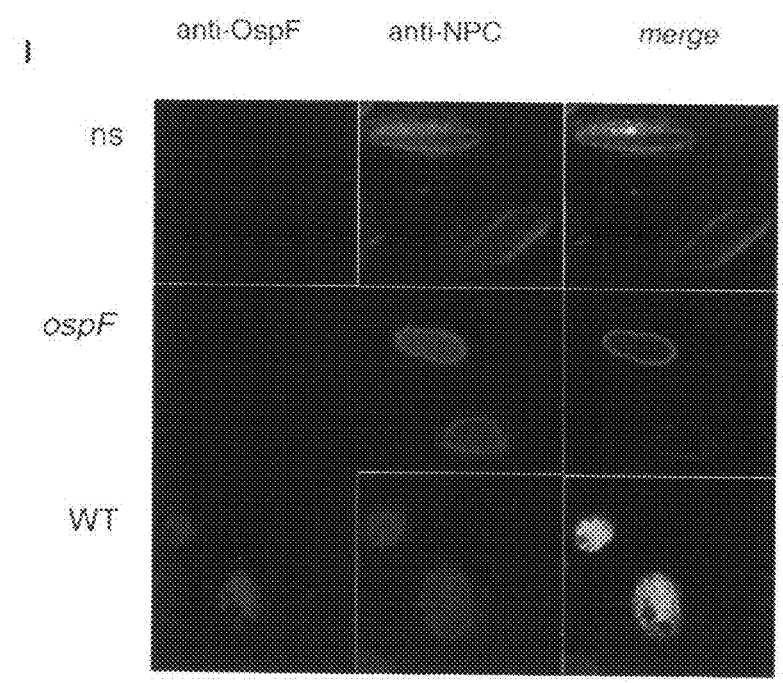

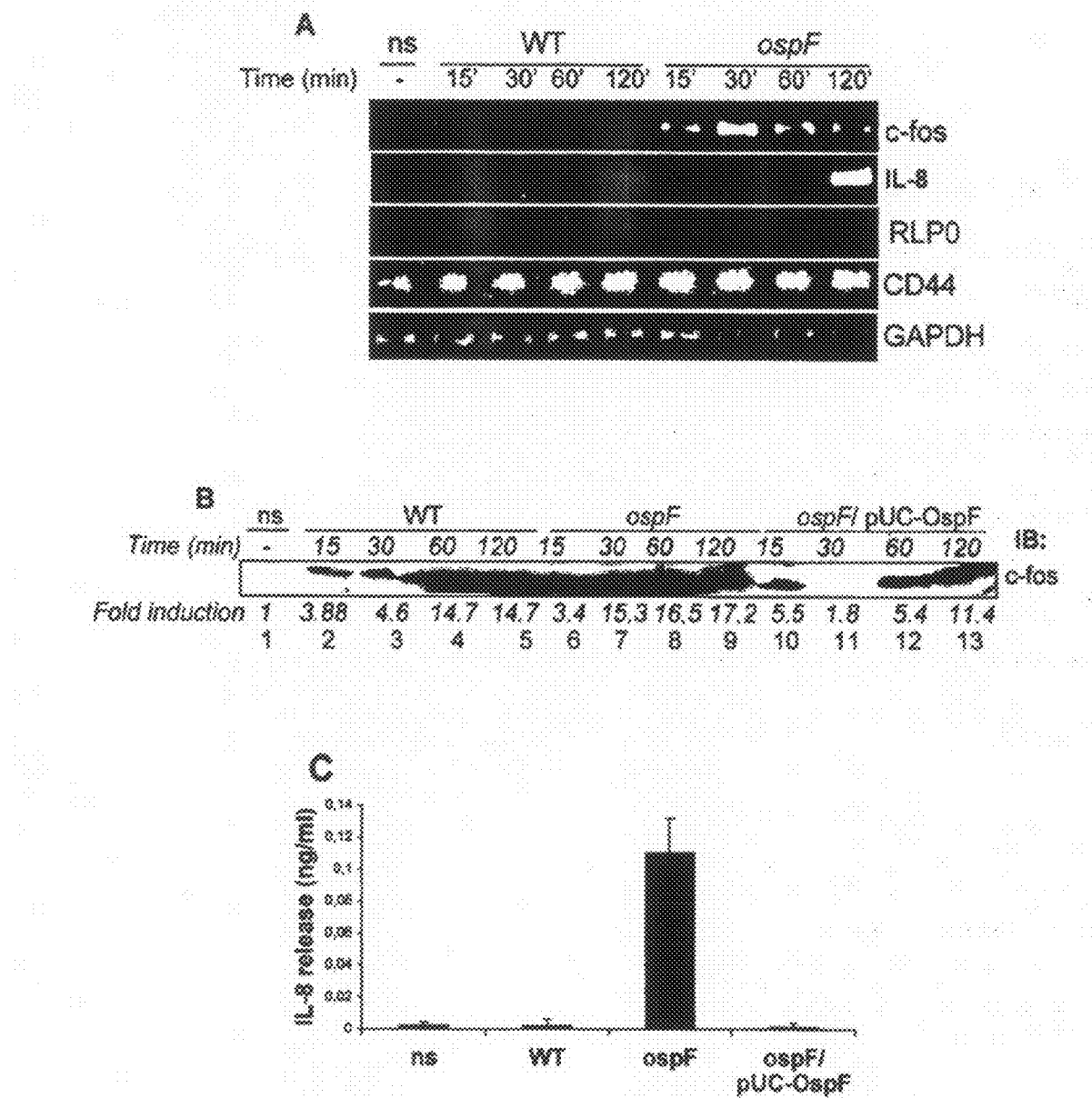

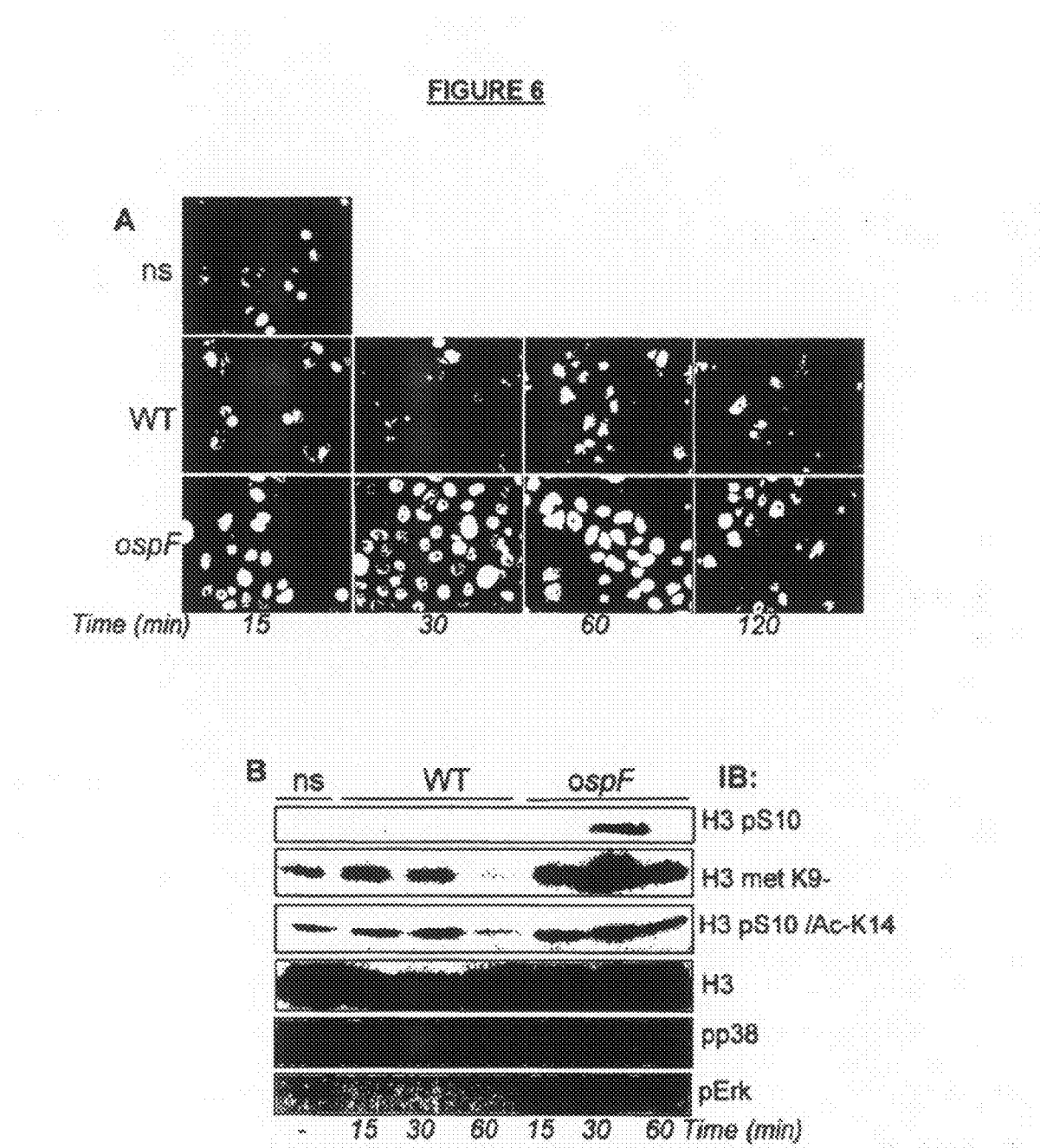

FIGURE 6 CONTINUED
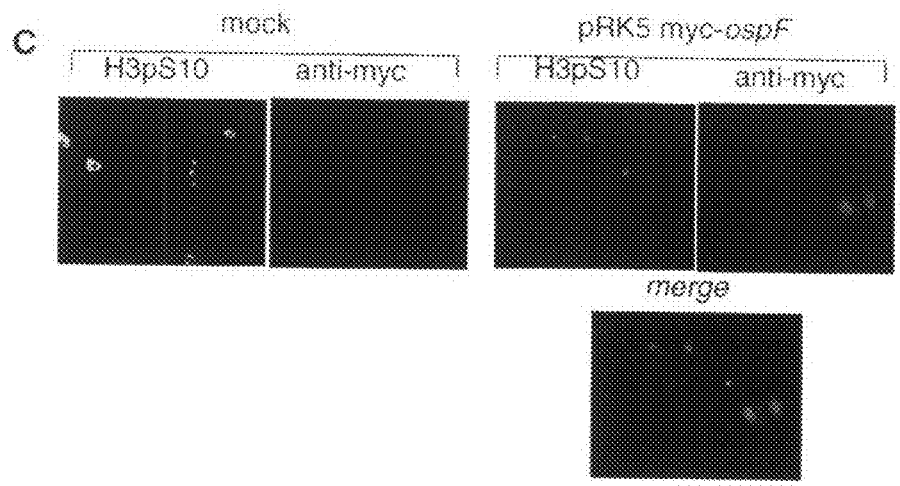
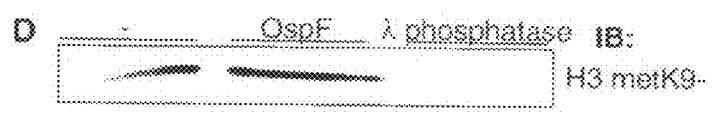
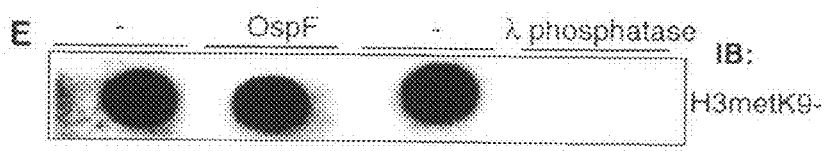

FIGURE 6 CONTINUED
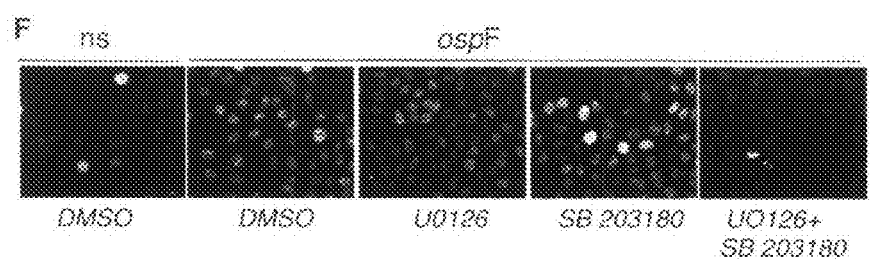
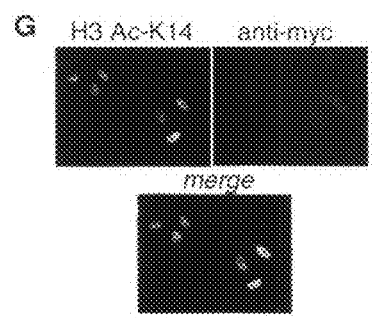

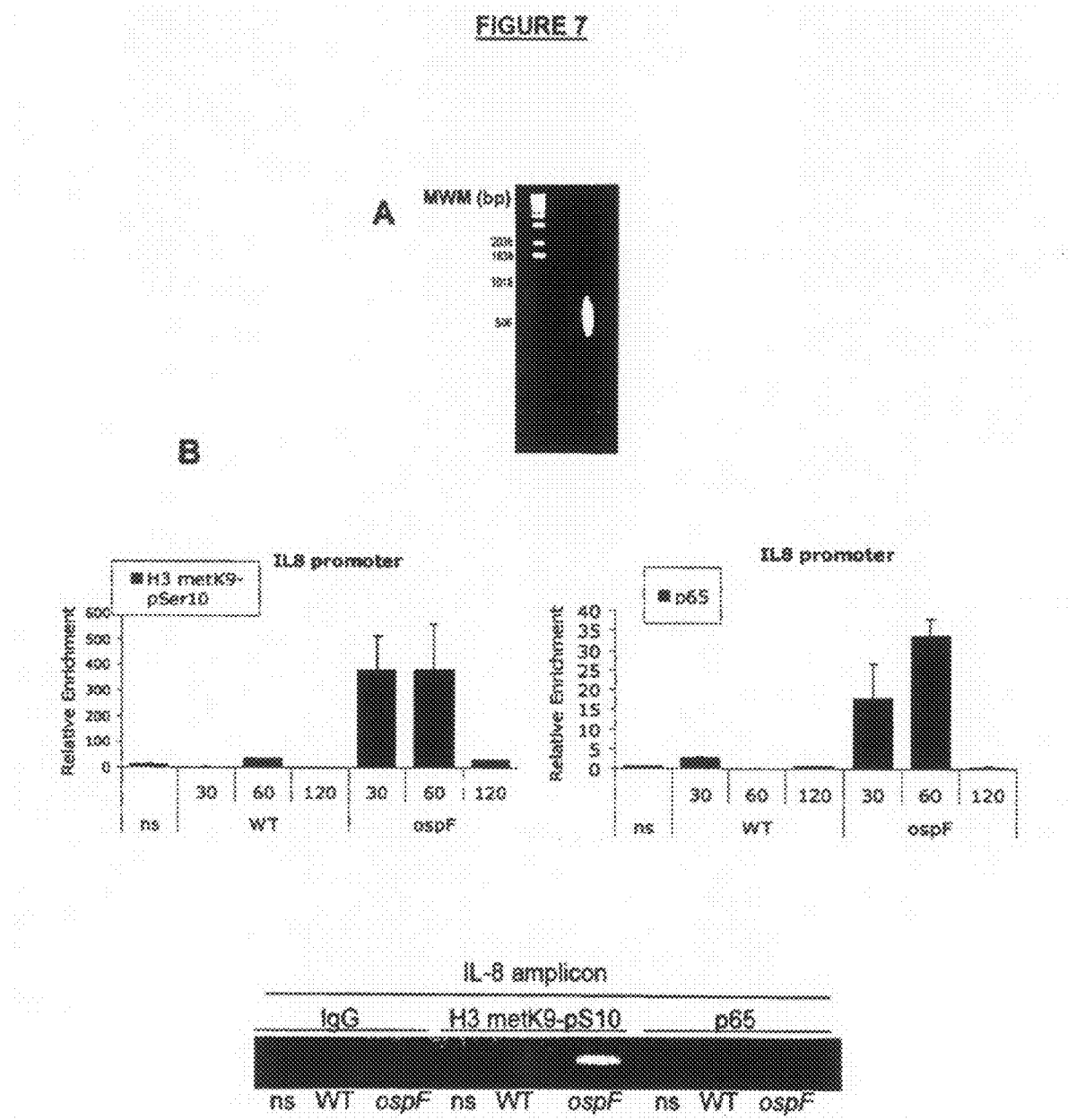

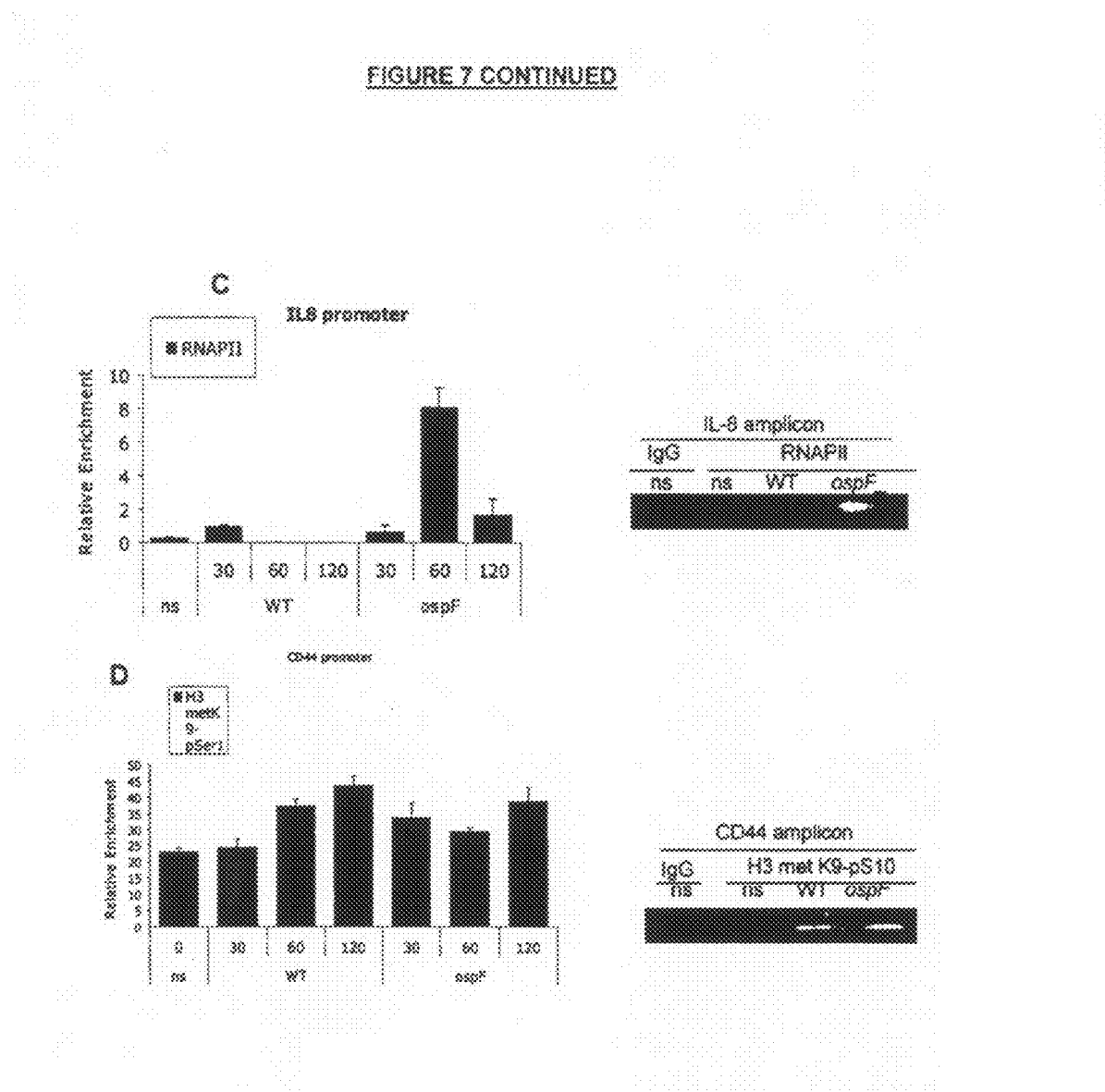

FIGURE 7 CONTINUED
F
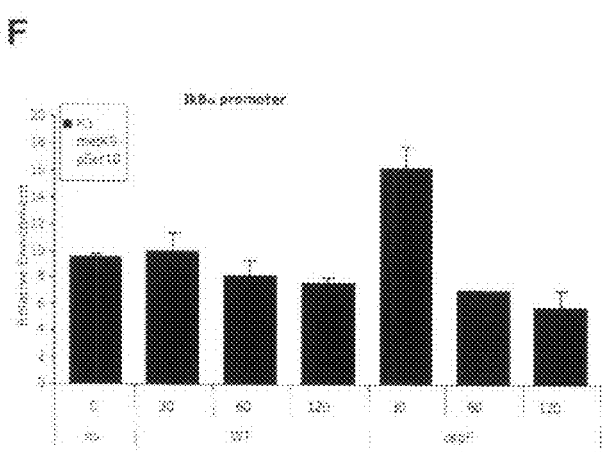
G
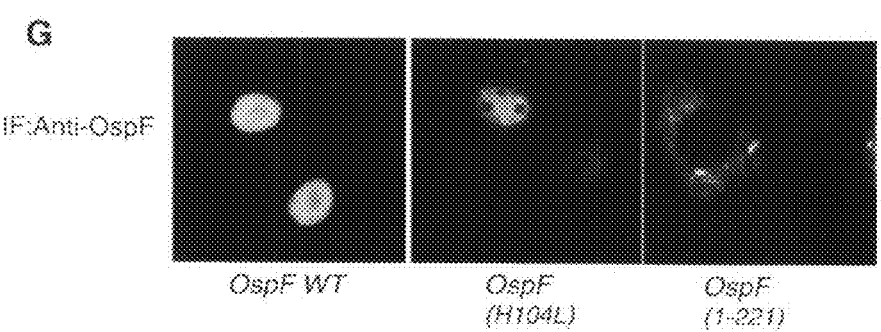

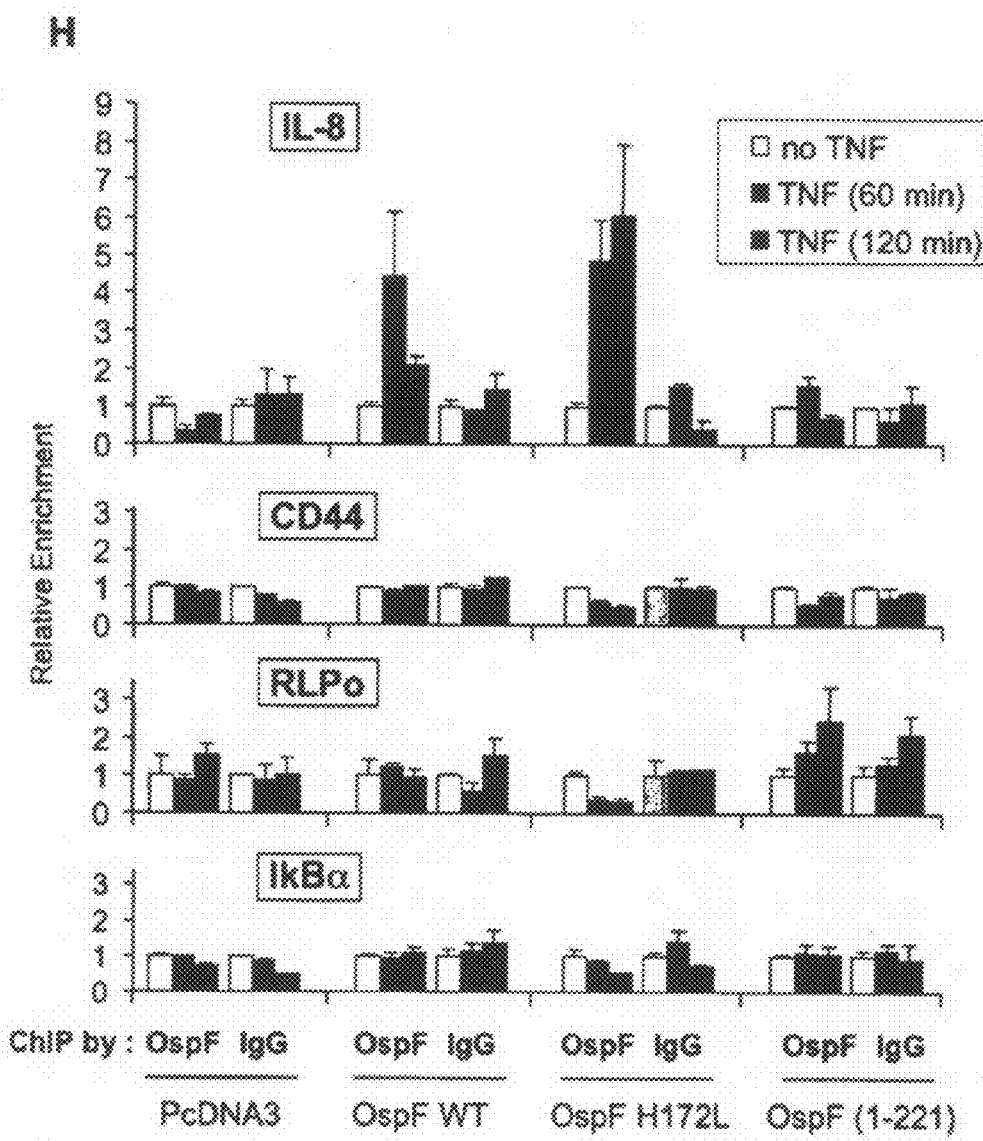

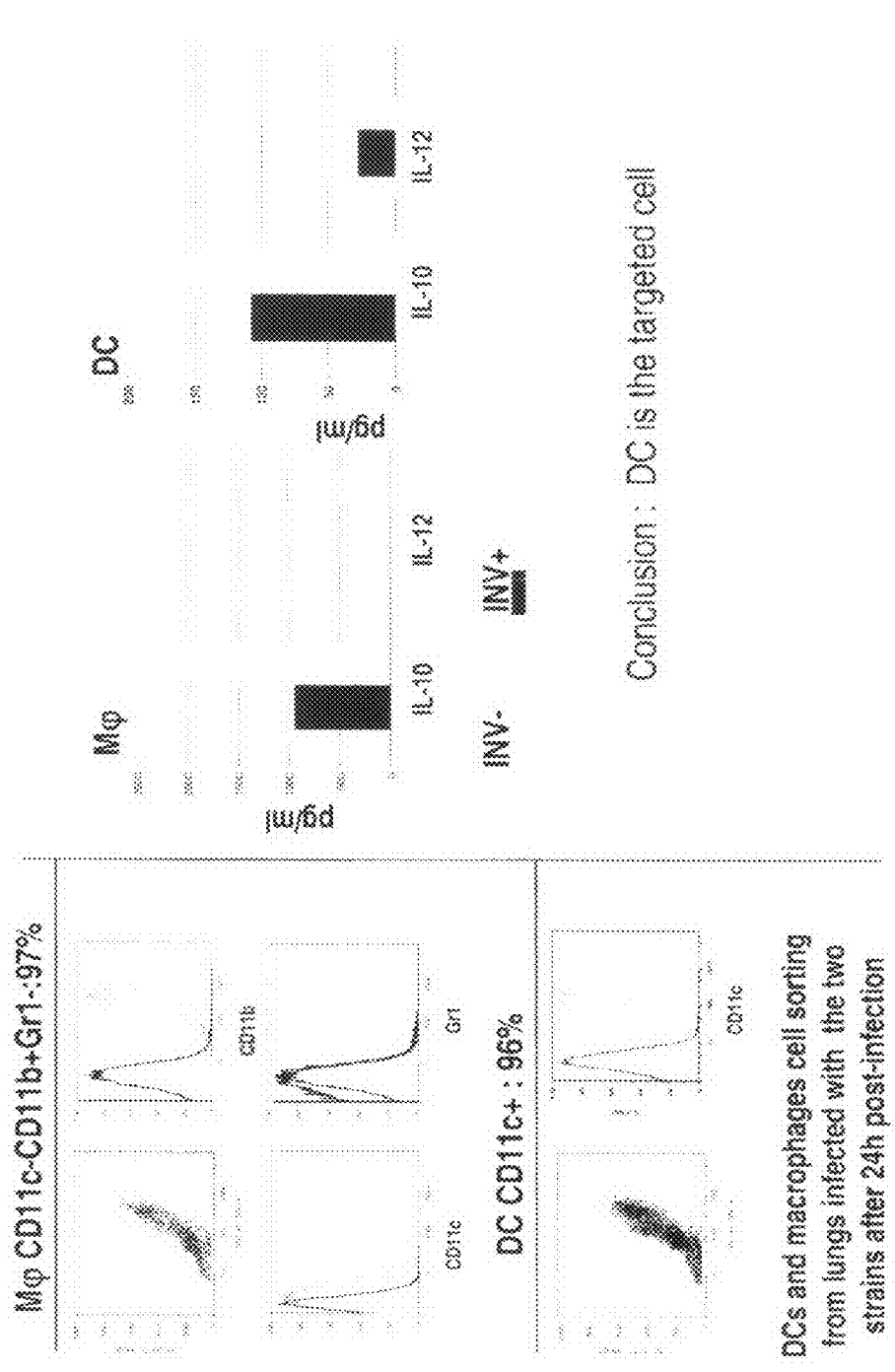

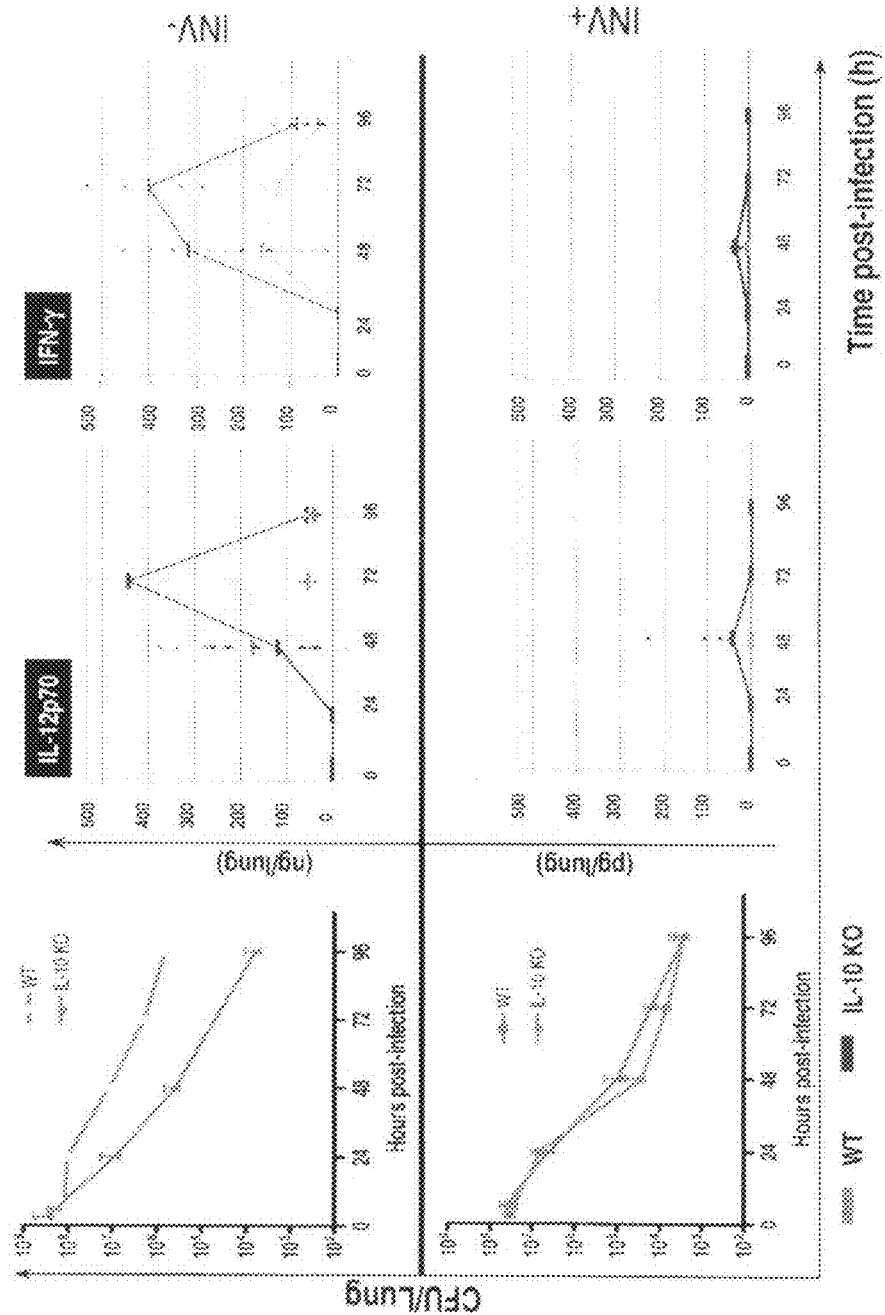

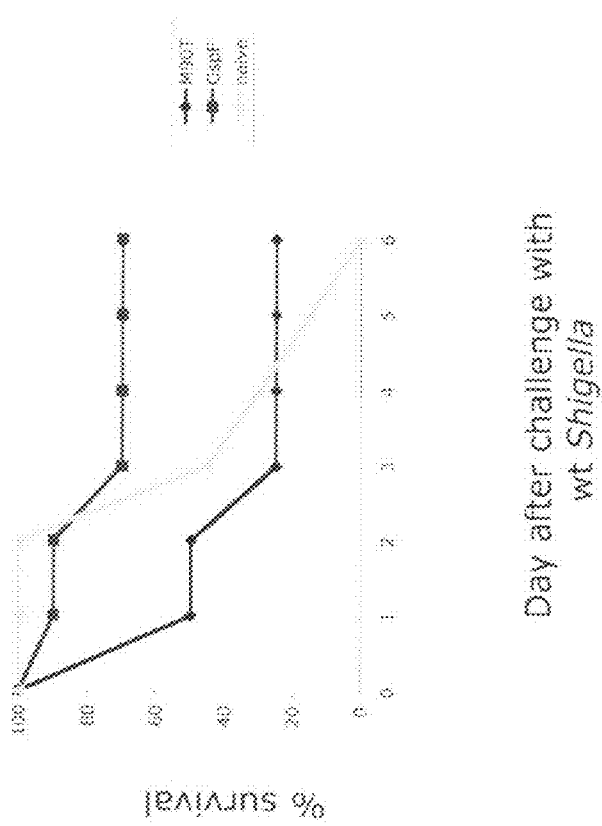

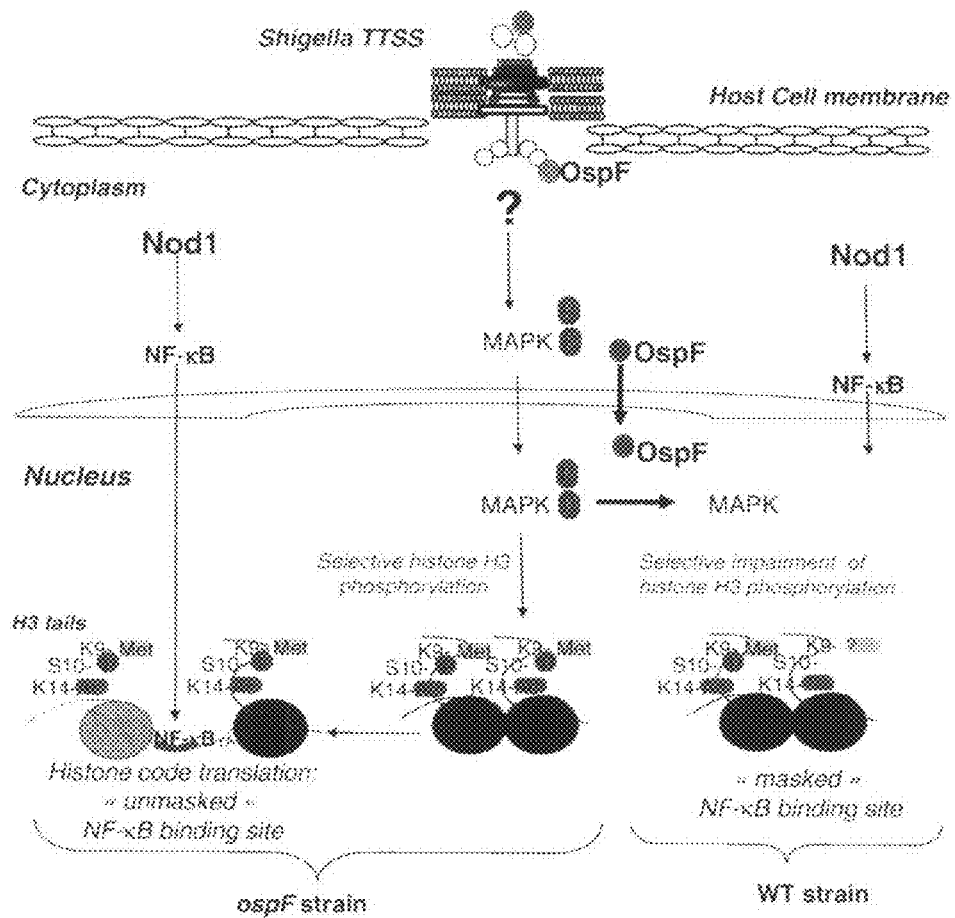

```
PsyrT  DC3000    ------MLALKLNTSIAQAPLKKNAEAELRHMNHAEVRAHTPT  50
PsyrB728A        ------------------- MKKDAGAQLRRLNQSEVRANRANTPT
VirA             MPINRAGLKLSLPSLNVGPVSERPQMSATNEDLKTNFHSLHNQMRQMPMS
SpvC             MPINRPNLNLNIPPLNIVAAYDGAEIPSTNKHLKNNFNSLHNQMRKMPVS
OspF             MPIKKPCLKLNLDSLNVVK.SEIPQMLSANERLKNNFNILYNQIRQYPAY PsyrT            RFTLNHRAPTY.EVAQSALGENHGGWTAVNKFKVTESEVFIHMERSDSRS  100
PsyrB            RFAVNHRAPTY.DVAQSALGENHGGWTAANHFKMTGSEVFIHMDRLEPNC
VirA             HFREALDAPDYSGMRQSGFFAMSQGFQLESH....GGDVFMHAHRENPQC
SpvC             HFKEALDVPDYSGMRQSGFFAMSQGFQLNNH....GYDVFIHARRESPQS
OspF             YFKVASNVPTYSDICQF.FSVMYQGFQIVNH....SGDVFIHACRENPQS PsyrT            KGDFAGDKIHLSVAPQHVASAFNAIGKILQADDSPVDKWKVTDMSCASSD  150
PsyrB            KGEFAGDKIHLSVAPEDVPHAFNAIGKTLQASDSPVDSWKVTDMKCLQAE
VirA             KGDFAGDKFHISVQREQVPQAFQALSGLLFSVDSPIDKWKVTDM.....E
SpvC             OGKFAGDKFHISVLRDMVPQAFQALSGLLFSEDSPVDKWKVTDM.....E
OspF             KGDFVGDKFHISIAREQVPLAFQILSGLLFSEDSPIDKWKITDM.....N PsyrT            LQPEKKRVTQGAQFTLYAKPDRADNTYSPEYMGKMRGMISSIERELHTAG  200
PsyrS            MPAAEQRVALGAQFTIYAKPDRADNTYSPEYMGKMRGMISSIEQELSAAG
VirA             RVDQQSRVAVGAQFTLYVKPDQENSQYSASSLHNTRQFIECLESRLSESG
SpvC             KVVQQARVSLGAQFTLYIKPDQENSQYSASFLHKTRQFIECLESRLSENG
OspF             RVSQQSRVGIGAQFTLYVKSDQECSQYSALLLHKIRQFIMCLESNLLRSK PsyrT            VQQSNNRPASDVAPGHWAYASYRNEHRSERAGSSSQANELEKEPFFQLVSF  251
PsyrS            VRQSSHRPDSDVSPGHWSYASYRNEHKSNRSGTSNQHRNLEAEPFFQLVSF
VirA             L.MPGQYPESDVHPENWKYVSYRNELRSGRDGGEMQSQALREEPFYRLMAE
SpvC             V.ISGQCPESDVHPENWKYLSYRNELRSGRDGGEMQRQALREEPFYRLMTE
OspF             I.APGEYPASDVRPEDWKYVSYRNELRSDRDGSERQEQMLREEPFYRLMIE PsyrT            PDVAASPVKSGASSRSLMPPPWTR  275
PsyrS            SDGASGSSRSSADHQALLPPPWAR
VirA             ------------------------
SpvC             ------------------------
OspF             ------------------------
```

US 8,092,989 B2

TARGETING THE HISTONE CODE AS A BACTERIAL STRATEGY FOR SELECTIVELY MODULATING GENE EXPRESSION

This application claims the benefit of U.S. provisional application No. 60/716,931, filed on Sep. 15, 2005, which is incorporated herein by reference.

FIELD OF THE INVENTION

This invention relates to a member of a new class of dual specific phosphatases, methods for treating diseases using the phosphatase, methods for identifying agents that modulate the phosphatase's activity, methods for identifying agents that mimic the phosphatase's activity, a method for regulating an immune response, and immunogenic compositions comprising the phosphatase. The invention also relates to a strain of *Shigella flexneri* containing an inactivated ospF gene and a vaccine comprising a strain of *Shigella flexneri* containing an inactivated ospF gene.

BACKGROUND OF THE INVENTION

*Shigella flexneri* is a Gram-negative bacterial pathogen that causes bacillary dysentery in humans by infecting epithelial cells of the colon. *Shigella* primarily infects intestinal epithelial cells (IECs) (Jung et al., 1995). *Shigella* expresses several proteins that provide a mechanism for delivering effectors that induce bacterial uptake into the host cell via phagocytosis. These proteins form a type III secretion system (TTSS) and are encoded by a 220-kb virulence plasmid. *Shigella* bacteria then gain access to the cytoplasm by lysing the phagocytic vacuole and then expressing a motility phenotype that allows infection of other cells nearby.

To establish a successful infection, *Shigella* must finely regulate the host's immune response, especially those responses leading to inflammation. In contrast to *Salmonella typhimurium*, *Shigella* is inefficient at invading the apical pole of polarized IEC. Instead, *Shigella* requires transmigration of polymorphonuclear leucocytes (PMN) to disrupt the epithelial barrier, facilitating cell invasion via the basolateral pole of epithelial cells (Perdomo et al., 1994). The host's inflammatory response, facilitated by cells of the innate immune system, attracts PMNs to the site of inflammation. Therefore, triggering inflammation at the early stage of infection is required for cell invasion by *Shigella*. Bacteria that reach the intracellular compartment of IEC grow and spread from cell to cell, protected from host immune defences. But infected IEC play a large role in the inflammatory process, both as sentinels that detect bacterial invasion and as a major source of mediators, particulary cytokines and chemokines that mediate the inflammatory response. These mediators include cytokines and chemokines that initiate and orchestrate mucosal inflammation (Jung et al., 1995). Bacterial recognition by IEC occurs essentially intracellularly via a cytosolic molecule, Nod1/CARD4 that senses a microbial motif, the peptidoglycan (Girardin et al., 2003). Nod1 activation induces other proinflammatory signalling pathways including NF-κB and c-Jun N-terminal kinase (JNK) that lead to the expression of chemokines (Philpott et al., 2000), such as interleukin 8 (IL-8). These chemokines are crucial for pathogen eradication (Sansonetti et al., 1999). Thus, triggering excessive inflammation is detrimental to *Shigella*'s survival in the host. To survive, this bacteria has evolved strategies for modulating transcription of proinflammatory genes.

Although plant and animal pathogens have developed various strategies for suppressing immunity, translocation of effector proteins via a TTSS is a mechanism by which many bacterial pathogens take control of the host innate immune response. The *Shigella* type III secreted OspG molecule has been shown to antagonize degradation of IκB-α by blocking its ubiquitinylation, thus demonstrating the potential of the microorganism to regulate the inflammatory response (Kim et al., 2005). Some TTSS effectors like YopE, T, and H from *Yersinina pseudo tuberculosis* primarily target actin polymerization as a way to escape phagocytosis (Cornelis, 2002), and other TTSS effectors suppress proinflammatory defense responses mediated by the innate immune response. In the latter case, many of these effectors are cysteine proteases that target essential components of defence signalling pathways. For example, the *Pseudomonas syringae* effector AvRpt2 initiates elimination of the *Arabidopsis* RIN4 protein, a regulator of basal defence (Axtell and Staskawicz, 2003). Other effectors induce reversible protein modifications: YopJ/P/AvrBsT represent a family of cysteine proteases that cleave the carboxy-terminus of the ubiquitin-like protein SUMO from the target proteins, and thereby interfere with multiple signalling pathways (Orth et al., 2000). YopJ also acetylates various kinases in their activation loop domains, thereby interfering with multiple signalling pathways (Mukherjec et al., 2006). The mechanisms behind how these effectors modify expression of specific host genes is currently unknown.

SUMMARY OF THE INVENTION

*Shigella* requires an inflammatory response to begin infection of host cells, but at the same time the bacteria would be eradicated if a strong inflammatory response ensues. Thus, it is to the bacterium's advantage to regulate genes that participate in the inflammation response and ultimately in chemokine expression that will influence the adaptive immune response towards a humoral response rather than a cellular response. The inventors sought to determine a mechanism by which *Shigella* regulates the expression of these host genes and in the process identified a phosphatase that is a member of a new class of dual specific phosphatases (DSPs).

The ospF gene is located on *Shigella*'s virulence plasmid (Buchrieser, 2000). Until now, the function of the protein encoded by this gene was unknown. The invention reveals that ospF encodes a phosphatase. Amino acid sequence comparison between mammalian DSPs reveals similarities within and immediately around a catalytic active site sequence motif, His-Cys-Xaa$_5$-Arg-Ser/Thr. This signature sequence motif is also in all tyrosine phosphatases described in other eukaryotes and in prokaryotes (Kennelly, 2001). Strikingly, the phosphatase encoded by the ospF gene, OspF phosphatase, does not contain this signature sequence, nor does it show significant sequence similarity with any DSP or other tyrosine phosphatases. Thus, OspF phosphatase is a member of a new class of DSPs. An understanding of the mechanisms by which *Shigella* regulates host gene expression can lead to more effective treatments for dysentery caused by *Shigella* and treatments for diseases that are mediated by the host genes that OspF phosphatase regulates.

The Examples provided herein show that the ospF gene encodes a phosphatase and that this phosphatase can interfere with signalling pathways involving extracellular signal regulated kinases (Erks) and mitogen-activated protein kinases (MAPKs). The Examples below also show that OspF phosphatase can decrease the transcription of a variety of host genes, including those encoding c-fos and IL-8. For IL-8 expression, the Examples demonstrate that the OspF phosphatase decreases transcription of the IL-8 gene by preventing changes in chromatin structure needed to allow transcription proteins like NF-κB and RNA polymerase II (RNAPII) to access the IL-8 promoter. Furthermore, the Examples also show that OspF phosphatase can downregulate the expression of interleukin 12 (IL-12), leading to a Th2 type adaptive immune response.

Based on this understanding, the invention provides methods for treating diseases using OspF phosphatase, methods for identifying agents that modulate OspF phosphatase's activity, methods for identifying agents that mimic OspF phosphatase's activity, methods of regulating an immune response, and immunogenic compositions comprising OspF phosphatase. The invention also relates to a strain of *Shigella flexneri* containing an inactivated ospF gene, vaccines comprising this strain, and methods of treating dysentery.

Specifically, in certain embodiments, this invention provides a method for treating or preventing cancer in a mammal, comprising administering to the mammal a composition comprising OspF or a substance that mimics OspF activity. In certain embodiments, the invention also provides a method for treating or preventing an inflammatory disease comprising administering to a mammal a composition comprising OspF or a substance that mimics OspF activity. In certain embodiments, the invention provides a method for treating or preventing disorders associated with transplantation comprising administering to a mammal a composition comprising OspF or a substance that mimics OspF activity. In certain embodiments, the invention provides a method of regulating an immune response comprising administering to a mammal a pharmaceutical composition comprising OspF or a substance that mimics OspF activity.

In certain embodiments, the invention provides a method of screening for compounds that mimic OspF activity comprising:
 (A) adding a compound to a cultured cell;
 (B) incubating the cell for different times;
 (C) detecting one or more OspF protein regulation activities in the cell;
 (D) comparing the protein regulation activities of the compound with the protein regulation activities of OspF; and
 (E) identifying a compound that mimics OspF activity.

In certain embodiments, the invention provides a method of screening for compounds that modulate OspF activity in a cell, comprising:
 (A) adding a compound to a cultured cell;
 (B) incubating the cell for different times;
 (C) detecting one or more OspF protein regulation activities in the cell;
 (D) determining which compounds alter the one or more OspF protein regulation activities in the cell; and
 (E) selecting the compounds that modulate OspF activity.

In certain embodiments, the invention provides a pharmaceutical composition comprising OspF or a substance that mimics or that modulates OspF activity. In certain embodiments, the invention provides a strain of *Shigella flexneri*, wherein the ospF gene is inactivated. In certain embodiments, the invention provides a method of treating or preventing dysentery caused by *Shigella* infection comprising vaccinating a patient in need thereof with a strain of *Shigella flexneri*, wherein the ospF gene is inactivated. In certain embodiments, the invention provides an anticancer treatment, an anti-inflammatory treatment, or a treatment for disorders associated with transplantation, the treatment comprising a pharmaceutical composition comprising OspF or a substance that mimics OspF activity. In certain embodiments, the invention provides a method of treating or preventing a *Shigella* infection comprising administering a compound that decreases OspF activity to a patient in need thereof.

BRIEF DESCRIPTION OF THE DRAWINGS

This patent or application file contains at least one drawing executed in color. Copies of this patent or patent application publication with color drawings will be provided by the Office upon request and payment of the necessary fee.

FIG. 2 shows that OspF phosphatase is a dual specificity phosphatase that directly dephosphorylates Erk. (A) An in vitro phosphatase assay was performed using supernatants from various bacterial strains using phospho Erk2-GST as substrate. Western blot analysis was performed with anti phospho-Erk (pErk) antibody. (B) An In vitro phosphatase assay was performed using respectively a GST or Histine-tagged versions of OspF, OspG or IpaH fusions proteins. Western blot analysis was performed as in (A). (C) 500 ng of OspF was mixed with 50 ng of phospho Erk2-GST for 1 hour at 30° C. in presence or absence of 1 mM orthovanadate or 3 nM okadaic acid. Western blot analysis was performed using anti-phospho Threonine 183 ($pT^{183}$) and phospho Tyrosine 185 ($pY^{185}$) Erk antibodies. (D) Purified bacterially expressed Erk2 was phosphorylated by MEK1 as described in Example 1. Three micrograms of the $^{33}$P-labeled Erk2 was incubated with 1 µg of OspF or MKP1 for 30 minutes at 30° C. resulting in an increase in the gel mobility of the substrate as shown by SDS-PAGE. (E) Western blot verifying dephosphorylation of the $^{33}$P-labeled Erk2 at the $pT^{183}$ or $pY^{185}$ residues using a phospho-Erk2 antibody. (F) Steady state kinetic analysis of Erk2 dephosphorylation by OspF. The reactions were carried out in duplicate in the presence of 100 nM OspF (solid line) or MKP1 (dashed line) at 30° C. for 10 minutes with various concentrations of $^{33}$P-labeled Erk2 substrate. Release of inorganic phosphate was measured as described in Example 1 and the data fitted to the Michaelis-Menton equation using the software Kaleidagraph. (G) HeLa cells were transfected with increasing doses of pRK5 myc-ospF, ospF (H104L), ospF (H172L) and stimulated with PMA. Western blot analysis was performed using anti-phospho Erk (pErk), anti-Erk1/2, or anti OspF antibodies. (H) GST-OspF or GST-OspF fusion proteins were mixed with 50 ng pErk2-GST for 15 minutes at 30° C. Western blot analysis was performed as in (A). (I) Inhibition of OspF activity by various phosphate analogs. Fifty nanograms of pErk2-GST were preincubated for 10 minutes at 30° C. with 10 mM vanadate, beryllofluoride (combination of 1 mM sodium fluoride and 100 µM beryllium chloride), aluminum fluoride (combination of 1 mM sodium fluoride and 100 µM aluminum chloride).

FIG. 3 shows that OspF phosphatase selectively inactivates Erk and p38 MAPKs in vivo. (A) HeLa cells were transfected with increasing doses of pRK5myc-OspF and stimulated by PMA. Western blot analysis was performed using anti-phosphoErk (pErk) or anti-Erk1/2 antibodies. (B,C) HeLa cells were transfected with increasing doses of pRK5myc-OspF and stimulated by TNF. Western blot analysis was performed using in (B) anti-phospho p38 (pp38) or anti-p38 antibodies and in (C) anti-phospho JNK (PJNK) and anti-p46/p54 JNK antibodies. (D,E) Caco 2 cells were infected either with the wild type (WT), the ospF (ospF) or the transcomplemented strain (ospF/pUC-OspF). Western blot analysis was performed with in (D) anti-phosphoErk (pErk) or anti-Erk1/2 antibodies, in (E) anti-phospho p38 (pp38) or anti-p38 antibodies. (F) Caco-2 cells were infected either with WT, the ospF mutant, or the transcomplemented strain (ospF/puc-OspF). Western blot analysis was performed with anti-phospho JNK 1/2 (pJNK1/2) or anti-JNK1/2 antibodies. (G) In vitro phosphatase assay was performed using 50 nM pErk2-GST, phospho p38-GST or phospho JNK1 Histidine. Western blot analysis was performed as in part (A). (H) HeLa cells were left untreated (ns) or either stimulated by the WT or ospF strains at the indicated times. IF was performed with anti-OspF antibodies. (I) HeLa cells were left untreated (ns) or stimulated for 45 minutes by the WT or ospF strains. IF was performed with anti-nuclear pore complex (NPC) (red) and anti-OspF antibodies (green).

FIG. 6 shows that OspF targets phosphorylation of Histone H3 at Serine 10 in a MAPK-dependent manner. (A) HeLa cells were left untreated (ns) or infected with the WT or the ospF strain at the indicated time. Indirect immunofluorescence detection was performed with anti-phospho-histone H3 S10 polyclonal antibody. (B) HeLa cells were synchronized by a double thymidine block (2 mM thymidine) and left untreated (ns) or infected with the WT or the ospF strain at the indicated time. Immunoblots were probed with anti-H3 phospho S10 (H3 pS10), anti-H3 methyl K9-phospho S10(H3 metK9-pS10), anti-H3 phospho S10. acetyl-K14 (H3 p-S10/Ac-K14), anti Histone H3 polyclonal anti-pp38 and pErk antibodies. (C) HeLa cells were transfected with pRK5myc-OspF vector and treated with 200 nM okadaic acid for 3 hours. IF was performed with anti-myc (red) and anti-H3 methyl K9-pS10 (green) antibodies. (D, E) OspF does not directly dephosphorylate histone H3 at Serine 10. (D) One micogram of calf-thymus histone (Sigma) was incubated with 300 ng of His-OspF or with 120 U of λ phosphatase for 2 hours at 30° C. Western blot was performed with an anti-metK9-pS10 antibody. (E) One micogram of peptide metK9-S10 was spotted onto a nitrocellulose membrane that was incubated with buffers, 5 µg/ml of OspF, or 2000 U/ml of lambda phosphatase for 2 hours at 30° C. Western blot was performed with an anti-metK9-pS10 antibody. (F) HeLa cells were pretreated for 60 min with either the MEK1 inhibitor U0126 (10 µM) or the p38 inhibitor SB203180 (2.5 µM) or both. Cells were left untreated (ns) or infected with the ospF strain for 30 min. IF was performed with anti-H3 methyl K9-pS10 antibody. (G) HeLa cells were transfected with pRK5myc-OspF vector and treated with okadaic acid (200 nm) for 3 hours. IF was performed with anti-myc (red) and anti-H3 methyl K9-pS10 (green) antibodies.

FIG. 8 shows that cytokines were produced by macrophage and dendritic cells (DC) recovered by cell sorting from lungs infected with the two strains after 24 hours post-infection. These cells were cultured ex vivo for 24 hours at 37° C. after which IL-10 and IL-12 production were measured by ELISA. The efficiency of cell sorting was measured by FACS.

FIG. 9 shows that WT and IL-10 knockout mice were infected with either the BS176 or M90T strains. At different time points post-infection, lungs were recovered. The bacterial load was measured with a plating assay while production of IL-12 and IFN-γ was measured by ELISA.

FIG. 11 provides the results of a protection assay. Three groups were analyzed. The first group was infected with the M90T strain, the second group was infected with the ospF strain, and the third group was infected with water (control group). Mice were vaccinated with $10^8$ bacteria per mouse and 3 weeks later the mice were boosted with $10^7$ bacteria per mouse. Eight weeks after boosting, the mice were challenged with a lethal dose of bacteria ($5 \times 10^8$ bacteria per mouse) and were monitored for survival.

FIG. 12 is a model showing that OspF targets the histone H3 at particular loci and modulates the extent of gene activation induced by proinflammatory signalling pathways. From the data obtained with the ospF strain, Shigella triggers, by a still unknown mechanism, a signalling pathway leading to MAPK activations. Both p38 and Erk kinases activities are required for inducing H3pS10. This phosphorylation occurs on histone H3 tails that are methylated on K9 and acetylated on K14, providing a histone code that promotes chromatin decondensation and recruitment of major components of the transcription machinery like NF-κB. The WT strain injects OspF through its TTSS. OspF inactivates MAP kinase within the nucleus and inhibits H3pS10 for selected genes. This modification promotes chromatin condensation and impairs promoter accessibility for the transcriptional machinery. The acetylation and methylation status of the histone H3 after infection by the WT strain are still unknown but OspF does not directly affect acetylation on K14.

FIG. 13 shows OspF phosphatase homology with other putative virulence proteins. Sequence alignment of OspF with two putative virulence proteins from Pseudomonas syringae Psyr T DC3000 (NP_790745) and Psyr B728A (ZP_00128143), VirA (NP_900978) from Chromobacterium violaceum, SpvC (NP_490528) from Salmonella enteritica serovar typhi. Identical amino acids are indicated in red and conserved substitutions in blue.

DETAILED DESCRIPTION OF THE INVENTION

Figure 1:
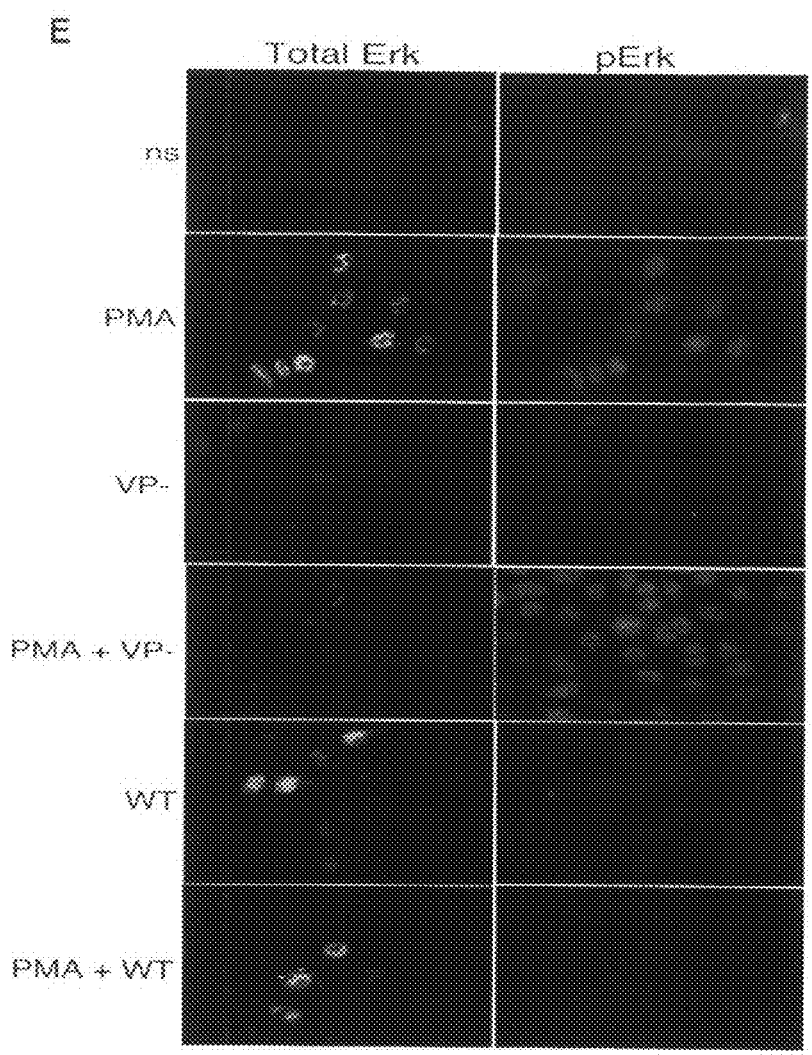
FIG. 1 shows that *Shigella* inactivates Erk within the nucleus. (A) HeLa cells were left untreated (ns) or either infected with the avirulent strain (VP-) or the virulent *Shigella* strain (WT) for the indicated times. Western blot analysis was performed using anti-phospho MEK1 (pMEK1), MEK1, phospho-Erk (pErk), Erk, phospho-c-Jun (pc-Jun), c-Jun or IκB-α antibodies. (B) HeLa cells were infected with the VP- or the WT strains and co-stimulated by PMA (1 µg/ml) for the indicated times. Western blot analysis was performed using anti-phospho Threonine 183 ($pT^{183}$) and phospho Tyrosine 185 ($pY^{185}$) Erk antibodies. (C) HeLa cells were stimulated by PMA or infected with the WT strain for the indicated times. Lysates were subjected to immunoprecipitation with MEK1 antibody and an in vitro kinase assay was performed using GST-Erk2 K52R as a substrate. Western blot analysis was performed with anti phospho-Erk (pErk) antibody. (D) HeLa cells were treated as in (C) for the indicated times. Lysates were subjected to immunoprecipitation with anti-Erk antibody and an in vitro kinase assay was performed using myelin basic protein (MBP) as a substrate. Western blot analysis was performed with anti-phospho Threonine 98 MBP (pMBP) antibody. The basal level of phosphorylated MBP is indicated with an asterisk. (E) HeLa cells were left untreated (ns) or either stimulated for 30 min by PMA, the VP strain, or the WT strain; or pre-treated for 15 minutes by PMA and infected during 15 minutes by the VP strain or the WT strain (PMA+WT). Immunofluorescence (IF) was performed with monoclonal anti-phospho Erk (red/right panels) and polyclonal anti-Erk antibodies (green/left panels).

Shigellosis, or bacillary dysentery, is a dysenteric syndrome caused by Shigella, a Gram-negative enterobacterium belonging to the Enterobacteriacae family. This human disease essentially occurs in developing countries, targeting children under the age of five. The molecular and cellular bases of the invasive process were largely studied over the last past years (Nhieu, 1999 and Parsot, 1994). A series of complex steps allows the bacterium to cross the intestinal barrier and invade intestinal epithelial cells, thus inducing an acute inflammation that leads to massive destruction of the intestinal barrier. Though inflammation plays an important role in the establishment of Shigella infection, a too vigorous inflammatory response could wipe out the infection. Thus, Shigella has evolved a mechanism for fine tuning the inflammatory response via a unique DSP, OspF phosphatase. As used herein, the terms "OspF phosphatase" and "OspF" refer to the protein encoded by the ospF gene. There are four Shigella species, namely S. flexneri, S. sonnei, S. dysenteriae, and S. boydii. In a preferred embodiment, Shigella is Shigella flexneri.

The sequence of the Shigella ospF gene was just disclosed in Buchrieser, 2000. The ospF gene, located on Shigella's virulence plasmid, encodes this phosphatase. Amino acid sequence comparison between mammalian DSPs reveals similarities within and immediately around a catalytic active site sequence motif, His-Cys-Xaa$_5$-Arg-Ser/Thr. This signature sequence motif is also in all tyrosine phosphatases described in other eukaryotes and in prokaryotes (Kennelly, 2001). Strikingly, the phosphatase encoded by the ospF gene (OspF phosphatase) does not contain this signature sequence, nor does it show significant sequence similarity with any DSP or other tyrosine phosphatases. Thus, OspF phosphatase represents a new class of DSPs. Few proteins of unknown functions from various proteobacteria exhibit similarity with OspF (FIG. 13): SpvC (63% sequence identity) encoded by the virulence plasmid of Salmonella enteritica serovar typhi, VirA (67% sequence identity) encoded by Chromobacterium violaceum, and two putative virulence proteins (40% sequence identities) from two strains of Pseudomonas syringae. The functions of these proteins are unknown.

Although primary structures of bacterial phosphatases are extremely diverse, comparative analysis shows that these proteins exhibit structural features similar to their counterparts in eukaryotes (Kennelly, 2001). To date, three distinct families of protein tyrosine phosphatases (PTP) have been identified having in common their catalytic mechanism and active site sequence: the conventional PTP, the low molecular weight PTP, and Cdc25 PTPs. Conventional PTPs, including YopH and SptP, display a high degree of selectivity for phospho-Tyr residues (Kennelly, 2001). IphP from the non pathogenic cyanobacterium Nostoc commune is the only described prokaryotic PTP sharing some functional and structural similarities with mammalian DSPs. This protein hydrolyzes both phospho-serine and phospho-tyrosine residues (Potts et al., 1993). Therefore, DSP in bacteria have been scarcely characterized and the biological relevance of such dual specificity remains unknown.

The lack of homology of similarity between OspF and others DSP argues against an eukaryotic origin for OspF. Nevertheless, the striking similarity of OspF with putative virulence proteins from others proteobacteria suggests the existence of a common ancestor that could have been acquired and maintained as a "selective advantage" for the bacteria. The IphP protein from the nonpathogenic strain of *Nostoc commune* is the only known DSP chromosomally encoded and its phosphatase activity may target endogenous bacterial proteins important for pathogen metabolism (Potts et al., 1993). By contrast, OspF is encoded by the 220-kb plasmid, which encodes the invasive phenotype of the species. It therefore represents the first DSP encoded by a virulence plasmid identified so far. When *Shigella* infects a cell, OspF is injected into the host cell and translocates into the nucleus where it mimics mammalian DSP function by dephosphorylating MAP kinases within the nucleus (FIG. 12).

The OspF protein sequence is known and is available at the National Center for Biotechnology Information (NCBI) database under Accession Number CAC05773. In certain embodiments, the invention provides a mutant strain of *Shigella* in which the ospF gene is disrupted to prevent OspF phosphatase expression by the mutant strain. This ospF mutant was deposited in the Collection Nationale de Cultures de Microorganismes (CNCM), 28, Rue du Docteur Roux, Paris, France under Accession Number CNCM I-3480 on Jul. 12, 2005, under the provisions of the Budapest Treaty. The invention also pertains to the use of this ospF mutant as a vaccine for treating or preventing dysentery caused by *Shigella* infection. In certain embodiments, the invention also provides a plasmid, puc-OspF, that expresses OspF. In certain embodiments, the invention provides a plasmid, pGEX4T2, that expresses an OspF-GST fusion protein. In certain embodiments, the invention provides a plasmid, pKJ-OspF, that expresses an OspF-histidine fusion protein. In certain embodiments, the invention provides a plasmid, pRK5myc-OspF, that expresses OspF with a myc label. The pRK5myc-OspF plasmid was deposited in the Collection Nationale de Cultures de Microorganismes (CNCM), 28, Rue du Docteur Roux, Paris, France under Accession Number CNCM I-3496 on Sep. 12, 2005, under the provisions of the Budapest Treaty.

OspF is a DSP in that this phosphatase can dephosphorylate two different amino acid residues, threonine and tyrosine. Many protein activities can be affected by the expression of OspF. As demonstrated in the Examples below, OspF regulates protein function via different mechanisms that effect signal transduction pathways and gene transcription, ultimately leading to the regulation of proteins involved in the immune response to *Shigella* infection.

The first mechanism involves direct inactivation of a protein by dephosphorylating one or more of its amino acid residues. For example, transcription factor AP-1 that regulates the expression of many pro-inflammatory genes is formed by homo or hetero-dimerization between the Jun and Fos family proteins. *Shigella* infection blocks the ability of phorbol myristic acetate (PMA) to induce AP-1 activation and represses the transcriptional induction of c-Fos through inactivation of MAPK Erk. Inactivation of OspF restores the ability of PMA to induce c-Fos expression and, as shown in the Examples below, OspF expression allows Erk migration from the cytoplasm to the nucleus upon *Shigella* infection. But Erk remains in its inactivated state in the nucleus due to dephosphorylation by OspF. OspF dephosphorylates the critical phosphothreonine and phosphotyrosine residues located within the activation loop of the kinase subdomain VIII of Erk. In addition, OspF demonstrates substrate specificity in that it inactivates Erk and p38 MAPK, but not JNK.

In the second mechanism, OspF prevents changes in chromatin structure that are needed to allow proteins that are part of the cell's transcription machinery to gain access to a gene's promoter. As the Examples demonstrate, OspF regulates IL-8 this way. Genes are expressed as a result of concerted processes of transcription, pre-mRNA processing, messenger ribonucleoprotein particle (mRNP) export and translation. Additionally, the transcriptional status of a gene is tightly linked to the structure of its chromatin. Packing of the eukaryotic genome into chromatin restricts the ability of many regulatory proteins essential for transcription to access genomic DNA. The amino-termini of the four core histones (H2A, H2B, H3 and H4) protrude out of the nucleosome, making these histones available for a variety of covalent post translational modifications including acetylation, phosphorylation, and methylation. These modifications alter the charged environment of the chromatin fiber or allow the histones to act as docking sites for chromatin remodeling factors and/or transcription factors regulating gene expression (Cheung et al., 2000).

Importantly, specific histone tail modifications can generate synergistic or antagonistic interaction affinities for chromatin-associated proteins, which in turn dictate dynamic transitions between transcriptionally active and transcriptionally silent chromatin sites. The modification status of histone proteins provides another layer or code of gene regulation beyond gene regulation that occurs at the transcription or translation level (for review see Jenuwein and Allis, 2001). This "histone code" thus determines the transcriptional state of a given gene.

For example, phosphorylation of Serine 10 on histone H3 tails already methylated on Lysine 9 favors the interaction with the chromodomain contained in heterochromatin protein 1 (HP1). However, in the context of acetylated Lysine 14, this phosphorylation event leads to delocalization of the protein, suggesting the formation of a histone code motif that may overcome HP1-mediated chromatin condensation and gene silencing (Mateescu et al., 2004). Serine 10 phosphorylation also occurs in a small fraction of H3 molecules associated with the promoters of Immediate Early (IE) genes like c-fos and a subset of NFκB-dependent pro-inflammatory cytokines and chemokine genes such as IL-8 (Clayton et al., 2000; Saccani et al., 2002; Clayton and Mahadcvan, 2003). In both cases, Serine 10 phosphorylation can be induced by Erk or p38 MAPKs signalling pathways, depending on the stimuli (Thomson et al., 1999). Importantly, MAPK-induced H3 phosphorylation occurs in a promoter-specific manner through a still unknown mechanism (Saccani et al., 2002). On these promoters, phosphorylation of histone H3 at Serine 10 creates a docking site for histone acetyl transferases (HATs) that in turn will acetylate the Lysine 14. These modifications may favor the binding of chromatin remodelling enzymes that increase promoter accessibility by disrupting the nucleosome structure (Saccani et al., 2002). The MAPK-dependent histone H3 phosphorylation therefore seems to be a key event for inducing chromatin remodelling at selective promoter sites, providing an efficient control strategy to selectively regulate the expression of a subset of NFκB-responsive genes involved in the immune response.

Indeed, as the Examples demonstrate, OspF regulates IL-8 expression by directly dephosphorylating Erk and p38 MAPKs within the nucleus, impairing histone H3 phosphorylation at Serine 10. OspF is injected into the target cell and translocated into the nucleus where it alters chromatin remodelling and the recruitment of essential components of the transcriptional machinery like NF-κB and the RNA polymerase II. Cell stimulation induces direct localizaiton of OspF to a selected promoter such as the IL-8 promoter, allowing OspF to prevent MAPK-dependent H3 phosphorylation in a gene-specific manner. Consistent with its ability to negatively regulate IL-8, OspF negatively regulates polymorphonuclear leukocyte recruitment and contributes to restricting bacterial invasion of intestinal cells. Alteration of the histone code by OspF allows *Shigella* to repress a selective pool of genes mainly involved in the immune response, providing a refined strategy to "carve out" a transcriptional response that best suits its needs for establishing an infection.

It is possible that histone H3 could be a direct substrate for DSP activity. However, it is more likely that OspF prevents histone H3 phosphorylation at Ser10 because of its ability to block both Erk and p38 MAPK pathways. Indeed, these 2 MAPKs are the two main activators of the nuclear kinase MSK (mitogen and stress-activated kinase), known to be a prominent histone kinase that directly phosphorylates histone H3 at Ser 10 (Thomson et al., 1999). As a result, *Shigella* can use OspF as a weapon that efficiently prevents formation of phosphorylated histone H3.

Importantly, this effect of OspF on histone H3 phosphorylation is not randomly distributed but targeted to specific promoters. This specificity may be a consequence of its ability to block MAPKs. MAPKs may be recruited to individual promoters via interactions with sequence-specific transcription factors, as shown for the *S. cerevisiae* p38.MAPK homolog Hog1 (Alepuz et al., 2001) and may initiate a signalling pathway leading to site-specific modifications. Additionally, a high resolution confocal microscopy approach has shown that activated MSK1 phosphorylates a specific set of histone H3 by a still unknown mechanism (Dyson et al., 2005), suggesting that the spatial distribution of the histone kinase to a particular loci may determine site-specific histone H3 phosphorylation. As a consequence, injecting OspF allows *Shigella* to repress a narrow set of genes, particularly those requiring chromatin decompaction at the promoter for successful gene transcription like IL-8.

For the IL-8 gene, it has been suggested that phosphoacetylation of histone H3 provides docking site for the bromodomain of chromatin remodelling proteins, that may participate in fully exposing the promoter and allow successful recruitment of NF-κB (Saccani et al., 2002). Generally, a bromodomain is a conserved protein domain able to recognize acetyllysine moiety in histone. The bromodomain is present in many chromatin remodeling proteins and interacts with the acetyllysine residue of histone. Results provided in the Examples fit with this model and indicate that formation of phosphoacetylated histone H3 methylated on K9 is a combinatorial pattern that promotes chromatin decompaction, thereby facilitating the concomitant recruitment of NF-κB and RNA polymerase II (RNAPII) at the promoter (FIG. 12).

Figure 4:
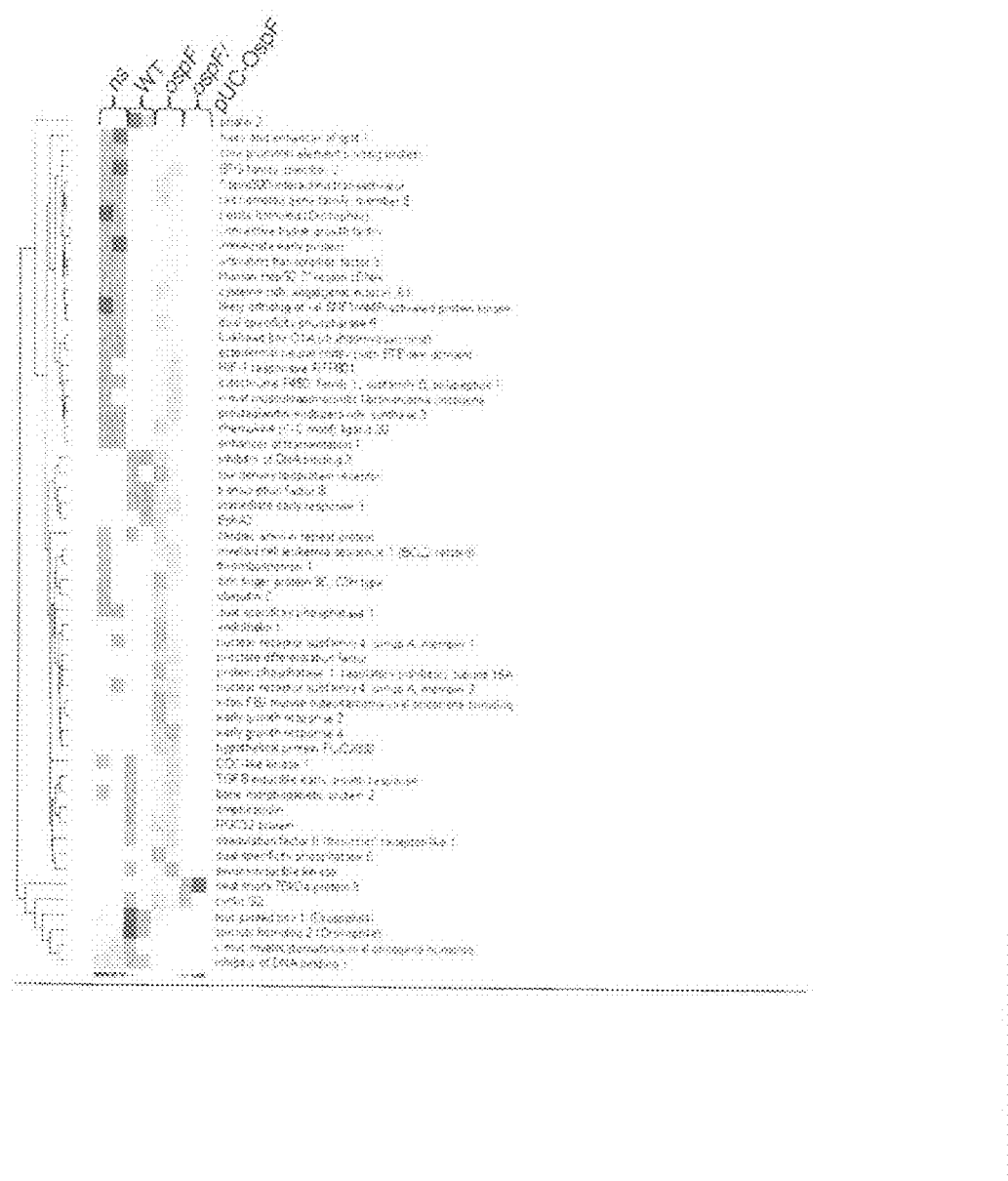
FIG. 4 shows a hierarchical clustering of the OspF-modulated genes in a gene array analysis. Caco-2 cells were infected for 2 hours with either the WT, ospF mutant, or the transcomplemented strain. Each row represents a gene and each column represents a sample. For the color scale, blue and red represent low and high signal expression values, respectively.
Figure 5:
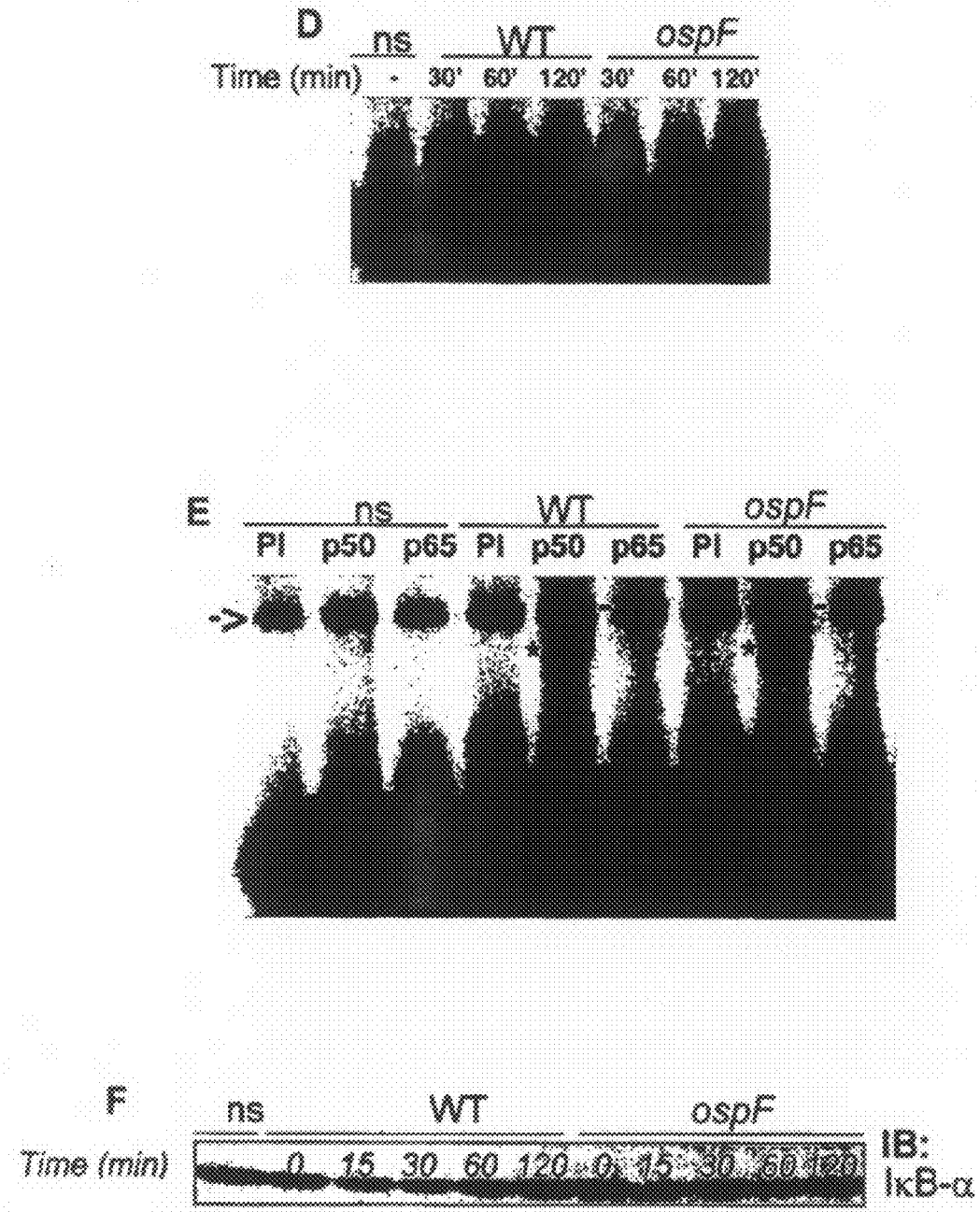
FIG. 5 shows that OspF is a transcriptional repressor that interferes with expression of crucial genes involved in the immune response. (A) RT-PCR time course analysis of mRNA expression in Caco 2 cells infected with the WT or the ospF strains at the indicated time. (B) Caco 2 cells were infected with WT or the ospF strains at the indicated time. Time course of c-fos protein expression analyzed by Western blot. (C) Caco 2 cells were infected with WT, ospF strain, or the transcomplemented strain for 5 hours. IL-8 secretion into culture supernatant was measured by enzyme linked immunosorbent assay (ELISA). (D, E) Caco 2 cells were infected with WT or the ospF strains. (D) Time course of NF-κB activation analyzed by gel shift assay. (E) A supershift assay was performed from nuclear extract from unstimulated cells (ns) or cells infected 1 hour with the WT or ospF mutant strains. Nuclear extracts were preincubated with the preimmune serum (PI) or p50 or p65 antibodies. The preimmune serum (PI) leads to a non specific band as indicated by an arrow. Anti-p50 supershift band (*) and anti p65 supershift band (−) are indicated. (F) Caco 2 cells were left untreated (ns), infected with the WT Shigella strain, or infected with the ospF strain at the indicated time. Western blot analysis was performed using an anti-IκBα antibody.

The gene array analysis of FIG. 4 shows that OspF specifically downregulates expression of major transcriptional activators such as AP-1, CREB, antiapoptotic proteins related to BCL2, and major proinflammatory genes like CCL20 and IL-8. AP-1 is a family of pro-inflammatory transcriptional factors comprising c-fos (referred to in FIG. 4 as v-fos FBJ murine osteosarcoma viral oncogene homolog). FIG. 5B also shows by RT-PCR that inactivation of OspF strongly upregulated c-fos mRNA expression. Overexpression or hyperactivation of the AP-1 transcriptional factor has been widely described in many cancers. For example, AP-1 is involved in colorectal cancer (Ashida, 2005).

Regarding CREB, ATF3 is a member of the CREB family of transcription factors and OspF down regulated its mRNA expression, as shown in FIG. 4.

Regarding antiapoptotic BCL2-related proteins, OspF down regulated the expression of MCL-1 (myeloid cell leukemia sequence), a member of the BCL-2 anti-apoptotic protein, as shown in FIG. 4. Upregulation of MCL-1 has been involved in various cancers, including lymphoma (Bai, 2006) and hepatocellular carcinoma (Fleischer, 2006). FIG. 4 also shows that OspF down regulated CCL20, also called chemokine (C—C motif) ligand 20. CCL20 is a dendritic cell (DC) chemoattractant that is known to play important roles in the control of bacterial dissemination by inducing interferon gamma production. CCL20 is also involved in the development of an efficient type 1 adaptive response. However, in inflammatory bowel disease (IBD), like Crohn's Disease (CD) or ulcerative colitis (UC) (Lee, 2005), activation of T cells by DC is thought to play a pivotal role in induction and maintenance of the disease. Therefore, expression of this chemokine was analyzed in IBD, its overexpression identified in the disease (Kaser, 2004).

Regarding IL-8, in the context of *Shigella*, IL-8 expression is crucial for bacterial eradication. As in IBD, an elevated intestinal IL-8 concentration that correlates with disease activity was found in both UC and CD (Nielson, 1997).

Figure 10:
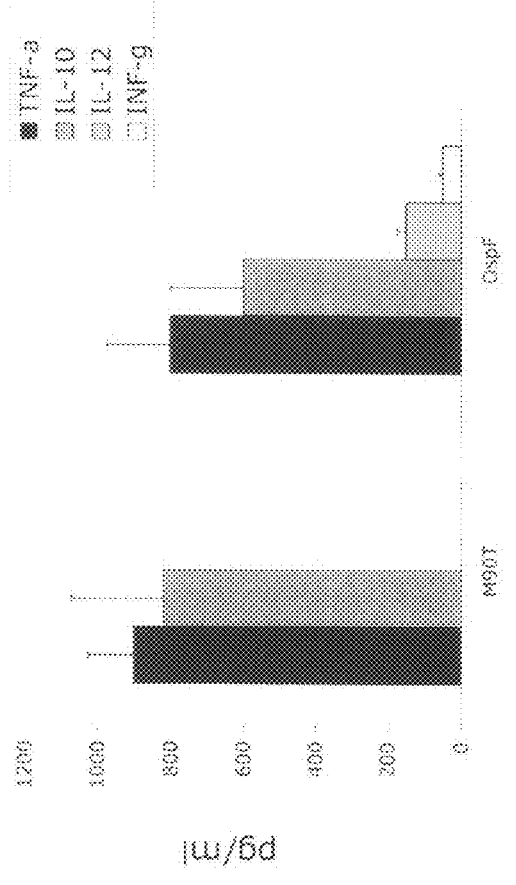
FIG. 10 shows that the production of cytokines from lungs infected with the M90T or the ospF strain at 24 hours post-infection were measured by ELISA after the recovery and the homogenization of the lungs.

As shown in FIG. 10, OspF also down regulated IL-12 production in vivo. It has been suggested that CD is associated with an exaggerated T-helper 1 cytokine response manifested by increased production of interleukin 12 (IL-12) (Schmidt, 2005). Anti-IL-12 antibodies are currently tested in clinical trials (Ardizzone, 2005).

In addition to affecting CCL20 expression and IL-8 expression, *Shigella* works in other ways to regulate the host's immune response. Innate immunity is essential for the recovery of primary infection, and plays a key role in the induction of adaptive immunity (for review see Janeway, 2002). Mammals are protected by innate immunity, that is, immune responses that generally act against invading pathogens and that include all aspects of immunity not directly mediated by lymphocytes. Cells such as phagocytic macrophage and natural killer cells mediate the innate response, which is distinct from "acquired immunity." Acquired immunity involves components of the immune system that are specific to a particular pathogen. These components include cellular immunity and humoral immunity. In cellular immunity, T cells respond to specific antigens presented by infected cells. In humoral immunity, B cells produce antibodies that bind to antigens on the specific pathogen. Cytokines and chemokines are one of the key links between innate and adaptive immunity (Mackay, 2001). Besides the induction of the inflammatory process, *Shigella* infection also induces specific humoral immunity. The humoral response is characterized by the production of specific secretory IgA (SIgA) at the intestinal level and IgG in blood serum (Phalipon, 1999).

Vaccine trials in humans using live attenuated vaccines showed that the intensity of the induced humoral response depends on the intensity of the inflammatory response elicited by the vaccine strain. In other words, a highly attenuated live vaccine candidate induces a weak inflammatory response and, therefore, a weak humoral response (for review see Phalipon, 2003). However, humoral protection induced upon natural infection with *Shigella* is of short duration, suggesting an inefficient priming of cellular immunity. The inventors investigated the impact of acute inflammation induced by *Shigella* upon primary infection on the development of specific immunity and protective immunity.

As shown in the Examples below, OspF acts as a transcriptional repressor in epithelial cells to control the pro-inflammatory response. OspF is also responsible for the control of IL-12 production, presumably by dendritic cells, observed at the early time point post-infection. OspF-induced IL-12 inhibition leads to the inhibition of IFN-γ production, a cytokine which is deleterious for *Shigella* infection. *Shigella*, inhibits the induction of an unfavorable Th1-type response to allow its survival within the host. This Th1-type pathway subsequently forces adaptive immunity towards a humoral response in the context of an immunosuppressive environment, since IL-10 is the main cytokine produced by the invasive strain at the early time post-infection. Thus, *Shigella* avoids the generation of a cellular immune response, which would be effective against bacterial infection.

Indeed, transcriptional analysis shows that OspF down regulates the expression of immune genes such as IL-8 and CCL20, and some pro-inflammatory early response genes such as the pro-inflammatory AP-1 family member c-fos and the genes encoding the Early Growth factors family members. OspF shares significant homology with two putative virulence proteins of unknown function from *Pseudomonas syringae* pv. *Tomato*. *P. syringae* is the causative agent of leaf blights and related diseases in many plants. Plant pathogens inject several type III effectors that were originally named avirulent (Avr) proteins because they were recognized by components of the plant defence system called Resistance (R) proteins. The R proteins share structural homology with mammalian receptors for pathogens including the Nod proteins and trigger plaint defence responses (Nurnberger et al., 2004). Interestingly, the *Pseudomonas Syringae* HopPtoD2 type III effector is a tyrosine phosphatase that can suppress the Avr-mediated plant immune response by a still unclear mechanism, suggesting a scenario in which pathogens have acquired the ability to avoid eukaryotic surveillance systems of the innate immune system by acquiring additional type III effectors that counteract the Avr signalling pathway (Espinosa et al., 2003). By analogy, *Shigella* may have acquired some type III protein effectors like OspF able to counteract the proinflammatory signalling pathway initiated by Nod1, providing a typical transcriptional signature in epithelial cells (FIG. 12).

The biological benefit for *Shigella* is its own survival since neutralizing IL-8 in vivo results in overgrowth of the bacteria in the lamina propria and a massive translocation through the intestinal epithelial barrier leading to the mesenteric blood (Sansonetti et al., 1999). However, IL-8 plays a key role in the early stages of *Shigella* infection because it is an important chemoattractant for polymorphonuclear leukocytes (PNN) that facilitates bacterial invasion via the basolateral pole of epithelial cells. Therefore, IL-8 transcriptional regulation by OspF may be temporally regulated. An elegant study has shown that pathogens can exploit the protein degradation machinery of the host in order to control the half-life of its own effector proteins, providing a temporal regulation of virulence effector function (Kubori and Galan, 2003).

In addition to OspF itself, the invention also provides for substances that mimic the activity of OspF. In certain embodiments, substances that mimic the activity of OspF will have one or more of the protein regulation activities described above. In certain embodiments, substances that mimic the activity of OspF will have two or more of the protein regulation activities described above. In certain embodiments, substances that mimic the activity of OspF will have three or more of the protein regulation activities described above. A protein regulation activity is the ability to regulate a protein's activity. Such regulation can be achieved via different mechanisms including, but not limited to, direct modification of the protein, such as, for example, dephosphorylation, or via regulation of the expression of the gene encoding the protein. A substance that mimics the activity of OspF is not limited to another protein but can also be, for example, a chemical substance. In some embodiments, protein regulation activities include, but are not limited to, regulation of the protein expression and/or activities of AP-1, CREB, RPA p32 (STAT activator), antiapoptotic proteins related to BCL2, and major proinflammatory genes like CCL20, IL-8, and IL-12.

A compound modulates OspF activity when the compound can increase or decrease at least one of the protein regulation activities of OspF. In certain embodiments, the invention provides a method of treating or preventing a *Shigella* infection comprising administering a compound that decreases OspF activity to a patient in need thereof. In certain embodiments, a compound which increases OspF activity is used in combination with OspF or a compound that mimics OspF in a pharmaceutical composition.

In some embodiments, a substance that mimics the activity of OspF is an OspF variant. As used herein, the term "OspF variant" refers to a protein having an amino acid sequence with one or more deletions, substitutions, or additions to the amino acid sequence of OspF. In some embodiments, a substance that mimics the activity of OspF is an OspF fragment. As used herein, the term "OspF fragment" refers to an OspF protein that has an amino-terminal and/or carboxy-terminal deletion. In certain embodiments, fragments are at least 5 to 238 amino acids long It will be appreciated that in certain embodiments, fragments are at least 5, 6, 8, 10, 14, 20, 50, 70, 100, 150, 200, or 238 amino acids long.

In some embodiments, a substance that mimics the activity of OspF is an OspF peptidomimetic. As used herein, the term "OspF peptidomimetic" refers to a compound containing non-peptidic structural elements, wherein the compound mimicks one or more of the biological properties of OspF. Such compounds are often developed with the aid of computerized molecular modeling. Peptidomimetics that are structurally similar to therapeutically useful peptides may be used to produce a similar therapeutic or prophylactic effect. Generally, peptidomimetics are structurally similar to a paradigm polypeptide (i.e., a polypeptide that has a biochemical property or pharmacological activity), such as OspF, but have one or more peptide linkages optionally replaced by a linkage selected from: —CH$_2$—NH—, —CH$_2$—S—, —CH$_2$—CH$_2$—, —CH=CH-(cis and trans), —COCH$_2$—, —CH(OH)CH$_2$—, and —CH$_2$—SO—; by methods well known in the art. In certain embodiments, systematic substitution of one or more amino acids of a consensus sequence with a D-amino acid of the same type (e.g., D-lysine in place of L-lysine) may be used to generate more stable compounds.

The ability of OspF to regulate the activity of Erk and p38 and immunomodulatory cytokines, such as IL-8, IL-12, and CCL20, suggests that OspF can provide beneficial treatments to patients afflicted with diseases involving Erk or p38 signal transduction and diseases involving inflammation. Such diseases include, but are not limited to, cancer, including but not limited to colonic cancer and pancreatic cancer, and Crohn's Disease. In a certain embodiment, OspF is used as an immunosuppressive agent to prevent or decrease the severity of transplant rejection. In certain embodiments, OspF is used to regulate an immune response.

In one embodiment, the invention provides a method for treating cancer in a mammal, comprising administering to the mammal a composition comprising OspF or a substance that mimics OspF activity to a patient having cancer, wherein treatment results in a reduction of disease. In one embodiment, the invention provides a method for preventing cancer in a mammal at risk for developing cancer, comprising administering to the mammal a composition comprising OspF or a substance that mimics OspF activity to a patient having cancer, wherein treatment results in prevention or delay in the onset of disease. Reduction of disease may be manifest by several indicators including a reduction in symptoms of the cancer, such as a reduction in fatigue or a reduction in tumour size. An effective amount is an amount that causes a reduction in symptoms or eradication of symptoms. The skilled artisan can determine what the appropriate dosage should be and the regimen of administration based on the type of disease involved, the stage of illness at the onset of treatment, and other factors, such as the patient's age and weight. In some embodiments, the invention provides an anticancer treatment comprising a pharmaceutical composition comprising OspF or a substance that mimics OspF activity. In some embodiments, the invention provides an anti-inflammatory treatment comprising a pharmaceutical composition comprising OspF or a substance that mimics OspF activity. In some embodiment, the invention provides a treatment for disorders associated with transplantation comprising a pharmaceutical composition comprising OspF or a substance that mimics OspF activity.

In some embodiments, the invention provides a method for treating inflammatory disorders comprising administering to a mammal an effective amount of a composition comprising OspF or a substance that mimics OspF activity. In some embodiments, the invention provides a method for preventing inflammatory comprising administering to a mammal at risk of developing an inflammatory disorder an effective amount of a composition comprising OspF or a substance that mimics OspF activity. Inflammatory disorders include, but are not limited to, Crohn's Disease, rheumatoid arthritis, osteoarthritis, inflammatory bowel disease, ulcerative colitis, multiple sclerosis, psoriasis, and proliferative lupus nephritis.

In some embodiments, the invention provides a method for treating disorders associated with transplantation comprising administering to a mammal an effective amount of a composition comprising OspF or a substance that mimics OspF activity. In some embodiments, the invention provides a method for preventing disorders associated with transplantation comprising administering to a mammal, who will receive a transplant, an effective amount of a composition comprising OspF or a substance that mimics OspF activity. Such disorders include, but are not limited to, graft-versus-host disease, complications resulting from solid organ transplantation, such as heart, liver, skin, kidney, lung (lung transplant airway obliteration) or other transplants, including bone marrow transplants and gene therapy.

In one embodiment, the invention provides a method of screening for compounds that modulate OspF activity in a cell, comprising:
  (A) adding a compound to a cultured cell;
  (B) incubating the cell for different times;
  (C) detecting one or more OspF protein regulation activities in the cell;
  (D) determining which compounds alter the one or more OspF protein regulation activities in the cell; and
  (E) selecting the compounds that modulate OspF activity.
In certain embodiments, the cells are chosen from HeLa cells, Caco 2 cells, and cells of the immune system. Cells of the immune system include, but are not limited to, T cells, B cells, and antigen presenting cells.

In one embodiment, the invention provides a method of screening for compounds that mimic OspF activity comprising:
  (A) adding a compound to a cultured cell;
  (B) incubating the cell for different times;
  (C) detecting one or more OspF protein regulation activities in the cell;
  (D) comparing the protein regulation activities of the compound with the protein regulation activities of OspF; and
  (E) identifying a compound that mimics OspF activity.
The OspF protein regulation activities in the cell include, but are not limited to, regulation of the protein expression and/or activities of AP-1, CREB, RPA p32 (STAT activator), anti-apoptotic proteins related to BCL2, and major proinflammatory genes like CCL20, IL-8, and IL-12. The skilled artisan can use techniques well known in the art to detect gene transcription regulation including Northern blots and PCR-based RNA detection. As the nucleic acid sequence encoding the proteins affected by OspF expression are known, the skilled artisan can routinely design PCR primers that will amplify part or all of the mRNA sequence of each protein target. The skilled artisan can also use well known techniques to detect dephosphorylation, such as the Western blot techniques used in the Examples below.

In some embodiments, pharmaceutical compositions comprise OspF and/or a substance that mimics or that modulates OspF activity and a pharmaceutically acceptable carrier. Pharmaceutically acceptable carriers are known in the art. In certain embodiments, the primary vehicle or carrier in a pharmaceutical composition may be either aqueous or non-aqueous in nature. For example, in certain embodiments, a suitable vehicle or carrier may be water for injection, physiological saline solution or artificial cerebrospinal fluid, possibly supplemented with other materials common in compositions for parenteral administration. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which may further include sorbitol or a suitable substitute therefor. In certain embodiments, a pharmaceutical composition is an aqueous or liquid formulation comprising an acetate buffer of about pH 4.0-5.5, a polyol (polyalcohol), and optionally, a surfactant, wherein the composition does not comprise a salt, e.g., sodium chloride, and wherein the composition is isotonic for the patient. Exemplary polyols include, but are not limited to, sucrose, glucose, sorbitol, and mannitol. An exemplary surfactant includes, but is not limited to, polysorbate. In certain embodiments, a pharmaceutical composition is an aqueous or liquid formulation comprising an acetate buffer of about pH 5.0, sorbitol, and a polysorbate, wherein the composition does not comprise a salt, e.g., sodium chloride, and wherein the composition is isotonic for the patient. Certain exemplary compositions are found, for example, in U.S. Pat. No. 6,171, 586. Additional pharmaceutical carriers include, but are not limited to, oils, including petroleum oil, animal oil, vegetable oil, peanut oil, soybean oil, mineral oil, sesame oil, and the like. Aqueous dextrose and glycerol solutions can also be employed as liquid carriers, particularly for injectable solutions. In certain embodiments, a composition comprising OspF, with or without at least one additional therapeutic agent, may be prepared for storage by mixing the selected composition having the desired degree of purity with optional formulation agents (*Remington's Pharmaceutical Sciences*, supra) in the form of a lyophilized cake or an aqueous solution. Further, in certain embodiments, a composition comprising OspF, with or without at least one additional therapeutic agents, may be formulated as a lyophilizate using appropriate excipient solutions (e.g., sucrose) as diluents. For example, the pharmaceutical composition can be an adjuvant in which OspF, in concert with other adjuvant components, regulates the immune response to an antigen.

Full citations for the references cited throughout this specification may be found at the end of the specification immediately preceding the claims. The disclosure of these publications in their entireties are hereby incorporated by reference into this application to describe more fully the art to which this invention pertains. To any extent that the teachings of the incorporated references may conflict with the teaching of this application, the application's teaching shall supersede the incorporated reference's teaching.

The following examples are presented to show that the ospF gene encodes a phosphatase and that this phosphatase regulates protein function via protein modification and transcription repression. These examples are meant to assist one of ordinary skill in using the OspF phosphatase and are not intended in any way to otherwise limit the scope of the disclosure.

Example 1

Materials and Methods

Cell Culture. The human intestinal epithelial cell line Caco-2, derived from a colonic carcinoma, and HeLa cells were used. Synchronization of the cells by a double thymidine block was performed as described previously (Harper, 2005).

Bacterial strains. The wild-type (WT) invasive strain of S. flexneri serotype 5a and a noninvasive variant (VP-) of the WT strain lacking the 220 kB virulence plasmid were used. The ipa mutants strains have been described previously (Mavris et al., 2002a). To construct the ospF mutant, a PCR amplified DNA fragment encompassing nucleotides 61 to 420 of ospF was cloned between the XbaI and EcoRI sites of the suicide plasmid pSW23T, generating pSWOspFTr. This plasmid was transferred by conjugation to the WT strain WT-Sm. A plasmid expressing the ospF gene was constructed by inserting a PCR fragment encompassing the ospF gene between the EcoRI and HindIII sites of pUC18, forming pUC18-OspF. This plasmid was used to complement the ospF mutant.

Plasmids and protein purification. The ospF coding sequence was amplified by PCR and cloned between the NcoI and BglII sites of pKJ1 to construct pKJ-OspF encoding OspF-His. Likewise, a PCR fragment carrying the ospF coding sequence was cloned between the BamHI and EcoRI sites of pGEX4T2 to construct pGEX4T2-OspF encoding GST-OspF. His- and GST-tagged OspF recombinant proteins were purified from derivatives of E. coli harboring pKJ-OspF or pGEX4T2-OspF. A PCR fragment carrying the ospF coding sequence was cloned between the BamHI and EcoRI sites of pRK5myc to construct pRK5myc-OspF encoding myc labelled OspF (myc-OspF). Point mutagenesis was generated according to the standard procedure of the Quick-Change site directed mutagenesis kit (Stratagene).

Indirect immunofluorescence. Cells were fixed with 3.7% paraformaldehyde in PBS for 10 min, permeabilized with 0.5% Triton-X in PBS. The following antibodies were used: anti-phospho-p42/p44 antibody (Sigma); anti-p42/p44, anti-phospho-histone H3 S10 (Upstate Cell Signaling), anti-acetyl histone H4 (Lys14) (Upstate Biotechnology) antibodies. The anti-H3 methyl K9-phospho S10 antibody was previously characterized (Mateescu et al., 2004). An anti-OspF antibody was generated by immunizing mice with the whole molecule according to the manufacturer (Eurogentec).

Preparation of the $^{33}$P-labeled Erk2 kinase substrate. The in vitro phosphorylation of the GST-Erk2 fusion protein was carried out by incubating 500 μg purified GST-Erk2 coupled to beads with 20 μg His6-tagged activated MEK1 (Upstate Cell Signaling) in a kinase buffer (50 mM Tris pH 7.5, 2 mM DTT, 10 mM MgCl$_2$) with 100 μM ATP (γ-3P ATP, 3000 Ci/mmol) for 2 hours at 30° C. The beads were washed 5 times with 30 ml of 1× PBS and eluted in 50 mM Tris pH 8, 10 mM glutathione, and 10% glycerol. The fractions were dialyzed overnight to remove residual ATP in 50 mM Tris pH8, 50 mM NaCl, and 10% glycerol.

In vitro phosphatase assay. The $^{33}$P labeled Erk2 phosphatase assay was performed in phosphatase assay buffer (0.1M sodium acetate, 50 mM Tris pH8) containing various concentrations of $^{33}$P-labeled Erk2 incubated with 100 nM OspF or MPK1 (Upstate Cell Signaling). In a preliminary experiment, the time course of 33P-labeled Erk2 dephosphorylation by OspF was determined and indicated that the maximal rate of hydrolysis of the substrate was reached at 10 minutes. Therefore, the reaction was initiated by the addition of the phosphatase, incubated for 10 minutes at 30° C. and terminated by adding 200 μl cold 20% trichloroacetic acid. The samples were centrifuged at 10,000×g and 200 μl of the supernatant was mixed with 5 ml of scintillation fluid for taking radioactivity measurements. The product generated (inorganic phosphate) was kept below 5% of the initial substrate concentrations. Reactions containing the Erk2 substrate and buffer without phosphatase was used as a blank for each data point. The data were fitted to the Michaelis-Menten equation using the software Kaleidagraph.

Kinases assays. Kinases assays were performed as described (Philpott et al., 2000). Five micrograms of Myelin Basic Protein (MBP) or 2 μg of the inactive form of Erk2, which has a Lys to Arg change at position 52 (Lys52Arg) (Upstate Cell Signalling) were used as substrates.

Gel shift and super shift experiments. Gel shift assays with nuclear extracts were performed as described (Philpott et al., 2000). For the supershift assay, nuclear extracts were incubated in the presence of anti-p50 (1141) and anti-p65 (1207-2) antibodies or irrelevant IgG.

Western Blot analysis. Solubilization of the histones were obtained by lysing the cells in Urea buffer (8M Urea, 10 mM tris pH7, 4, 1 mM EDTA, 1 mM DTT and proteases inhibitors). The following antibodies were used: anti-phospho Erk1/2, anti-phospho p38, anti-phospho-SAPK, anti-phospho MEK1/2 antibodies (Cell Signaling Technology), anti-phospho Threonine183 antibody (Promega) and anti-phospho Tyrosine 185 (Upstate Cell Signaling) Erk antibodies, anti-IκB-α antibody (Santa Cruz Biotechnology), anti-phospho (S10)-acetyl (K14) histone H3 polyclonal antibody (Upstate Biotechnology), and anti-histone H3 antibody (Abcam).

GeneChip hybridization and analysis. Synthesis, hybridization and labelling of RNA were performed as described (Pedron et al., 2003). Comparative analyses with dChip software (Li and Wong, 2001) between baseline (WT infected cells) and experiment (mutant strain or transcomplemented strain infected cells) were done with the dChip, using an unpaired Welch t-test with a p-value threshold of 0.05 and a Signal Log Ratio (SLR) threshold of 0.6. The SLR threshold corresponded to a fold change of 1.5. This software was also used for hierarchical clustering using Euclidian distance and average as a linkage method. Before clustering, the expression values for one gene across all samples are standardized to have a mean of zero. Increased or decreased values were then ranged compared to this mean.

Chromatin immunoprecipitation and Quantitative Real-Time PCR (QPCR). Formaldehyde-fixed Caco 2 cells were extracted to remove non-fixed components. Sonicated chromatin corresponding to 5×10⁶ cells was subjected to immunoprecipitation with 3 μg of irrelevant IgG, anti-H3 methyl K9-pS10, anti-p65 (1226) and anti-RNA polymerase II (SC899-Santa Cruz biotechnology) polyclonal antibodies. After extensive washes, crosslinking was reversed, and nucleic acids were isolated by the phenol/chloroform method. Aliquots were used for QPCR. QPCR was carried out with SYBR Green kits (Applied) according to manufacturer's instructions. The following promoter specific were used:

```
IL-8: sense
5'-AAGAAAACTTTCGTCATACTCCG-3'      (SEQ ID NO. 1)

anti-sense
5'-TGGCTTTTTATATCATCACCCTAC-3'     (SEQ ID NO. 2)

CD44: sense
5'-TCCCTCCGTCTTAGGTCACTGTTT-3'     (SEQ ID NO. 3)

anti-sense-
5'-CCTCGGAAGTTGGCTGCAGTTT-3'       (SEQ ID NO. 4)

hRLP0: sense
5'-ACAGAGCGACACTCCGTCTCAAA-3'      (SEQ ID NO. 5)

anti-sense
5'-ACCTGGCGAGCTCAGCAAACTAAA-3'     (SEQ ID NO. 6)

IκB-α: sense
5'-ATCGCAGGGAGTTTCTCCGATGA-3'      (SEQ ID NO. 7)

anti-sense
5'-GGAATTTCCAAGCCAGTCAGACCA-3'.    (SEQ ID NO. 8)
```

PCR samples were pre-incubated at 95° C. for 10 minutes followed by 45 cycles of 94° C. for 15 seconds, 60° C. for 50 seconds, and 72° C. for 60 seconds. The last cycles was followed by a final elongation incubation at 72° C. for 10 minutes.

In Vivo Infections and Histology. Rabbit intestinal loop infections were performed as described (Perdomo et al., 1994b). Suspensions of 5×10⁹ bacteria (0.5 ml) were injected into 5 cm rabbit small intestine loops. Loops were returned to the abdominal cavity, and rabbits were euthanized after 8 hours. Each bacterial strain was tested in three rabbits. Tissue staining with haematoxylin and histopathological analysis were performed as described (Perdomo et al. 1994b). Immunolabeling experiments were performed with an anti-S. flexneri 5a LPS antiserum and PMNs were stained with ant-NP5 antiserum (Pharmingen).

Example 2

Shigella Inactivates Erk and Sequesters Erk into the Nucleus

MAPK pathways play important roles in regulating gene expression in eukaryotic cells by phosphorylating transcription factors, co-regulators, and chromatin remodelling components. The three major subfamilies of MAPKs in mammalian cells include the Erk 1 and 2, JNK 1, 2, and 3, and p38 proteins (p38α/β/γ/ε). MAPK kinases (MAPKKs) activate MAPKs by phosphorylating threonine (Thr) and tyrosine (Tyr) residues at TEY sequences located in the MAPK's activation loop domain. MAPKKs are in turn activated by phosphorylation at serine (Ser) and Thr residues performed by MAPKK kinases (MAPKKKs). In quiescent cells, the two isoforms of MAPKs, Erk1 and Erk2, are inactive and retained in the cytoplasm via a direct association with their upstream activator, the kinase MEK1. Upon cell activation, activated MEK1 phosphorylates Erk1 and Erk2 on the TEY sequence leading to dissociation of the MEK-Erk complex before Erk translocates into the nucleus (Burack and Shaw, 2005). The following experiment demonstrates how Shigella modulates activation of MAPKs in HeLa cells.

HeLa cells were infected with the wild type invasive Shigella strain (WT) or the non-invasive VP-strain lacking the virulence plasmid. To verify the removal of the virulence plasmid, c-Jun phosphorylation was monitored. The invasive WT strain induced phosphorylation of the protein c-Jun, a major target of JNK kinase, while the non-invasive VP-strain did not induce phosphorylation of c-Jun (FIG. 1A, compare lanes 5 and 10). Infection with the WT strain also resulted in the degradation of IκB-α, providing evidence for activation of the IF-κB (IKK) pathway, as previously described (Philpott et al., 2000) (FIG. 1A, lanes 7-11).

The effect of Shigella infection on the phosphorylation of two kinases, MEK1 and Erk 1/2, was determined by using either antibodies specific for MEK1 dually phosphorylated on the two Ser residues ($S^{217}$ and $S^{221}$) in the activation loop of subdomain VIII or antibodies specific for Erk1/2 dually phosphorylated on the $T^{183}EY^{185}$ sequence. Shigella infection induced the formation of an active form of MEK1 phosphorylated on its two Serine residues (FIG. 1A, lanes 7-11). However, activated MEK1 failed to induce Erk phosphorylation (FIG. 1A). Moreover, as demonstrated with antibodies that detect either the phospho-Thr$^{183}$ (pT) or phospho-Tyr$^{185}$ (pY) residues of Erk 1/2, PMA, a potent activator of the Raf kinase, failed to significantly induce Erk phosphorylation on both residues in cells infected with WT. In contrast, cells infected with the VP-strain did show Erk phosphorylation (FIG. 1B, compare lanes 2-4 with 6-8). Taken together, these results suggested that the WT strain had the ability to interrupt the signalling pathway downstream from MEK1. Indeed, kinase assays confirmed that Shigella was a rapid and potent MEK1 activator (FIG. 1C, lanes 4-6) but was paradoxically unable to induce downstream enzymatic activation of Erk (FIG. 1D, lanes 5-7).

Shigella could inactivate Erk either by altering its spatial localization or by regulating a cellular phosphatase activity responsible for dual dephosphorylation of its critical phospho-threonine and tyrosine residues. In mammals, the MAP kinase phosphatases (MKPs) are DSPs which display substrate preference for various MAP kinases and occupy distinct subcellular compartments. Hence, whereas MKP-3 appears to be exclusively cytosolic, MKP-1 and MKP-2 are localized in the nucleus, resulting in the nuclear accumulation of Erk1/2 in its dephosphorylated form (Volmat et al., 2001). The subcellular localization of Erk after Shigella infection was assessed and compared to the localization of total Erk with that of active Erk. PMA stimulation induced a complete nuclear translocation of Erk in its active phosphorylated form (FIG. 1E). Interestingly, infection by Shigella induced nuclear accumulation of Erk but in its inactive dephosphorylated form. PMA stimulation performed in presence of Shigella led to unmodified Erk nuclear localization but the nucleus remained void of phosphorylated Erk. This effect was not observed in the course of infection with the VP-strain.

These results suggested that invasive Shigella could trigger a nuclear phosphatase activity targeting Erk once the protein has translocated into the nucleus. The mammalian MKP-1 or 2 which are possible candidates for Erk inactivation in the nucleus are neo-synthesized in response to various stimuli (Brondello et al., 1997). But Erk inactivation by Shigella was independent of new protein synthesis, as evidenced by cycloheximide treatment to block protein synthesis after Shigella infection. Based on these observations, a bacterial protein effector encoded by the virulence plasmid could be injected into the cells via the TTSS to induce Erk nuclear inactivation.

Example 3

The ospF Gene Encodes a Bacterial Phosphatase that Directly and Dually Dephosphorylates Erk Upon contact with the epithelial cell surface, the *Shigella* TTSS apparatus activates and approximately 20 proteins are secreted through this secretion. The TTSS apparatus is weakly active during bacterial growth in vitro at 37° C. and is deregulated by inactivation of the ipaB or ipaD genes (Menard et al., 1994).

Since the major Erk phosphatases described in mammals are soluble enzymes, a strategy was developed to identify a putative bacterial DSP using bacterial supernatants from deregulated mutant strains in which the ipaB gene has been either inactivated (ipaB2 strain) or disrupted, leading to a truncated version of the ipaB protein (ipaB4 strain) (Mavris et al., 2002a). Supernatants from these mutant strains were assayed for the phosphatase activity using a commercial phospho-Erk2-glutathione S transferase (pErk2-GST) fusion peptide as a substrate.

The supernatant from both ipaB mutants strongly dephosphorylated pErk2-GST (FIG. 2A, compare lanes 1-2 with 34). These results showed that a secreted bacterial protein could act as an Erk phosphatase. Inactivation of the ipaA, B, C, and D genes (ΔipaABCD mutant strain) did not impair dephosphorylation of the substrate by the supernatant (FIG. 2A, lane 6), indicating that IpaA-D proteins were not involved in this process.

The transcription of *Shigella* protein effectors is regulated by secretion activity under the control of MxiE is a transcription activator encoded by the virulence plasmid that belongs to the AraC family of transcriptional regulators. MxiE is required for the expression of 11 plasmid genes encoding secreted proteins (Mavris et al., 2002b). Interestingly, the supernatant of a ipaB4 mxiE double mutant strain was devoid of phosphatase activity (FIG. 2A lane 5). These results indicated that one of the 11 secreted proteins that are transcriptionally regulated by MxiE was a phosphatase.

Using purified proteins, three of those 11 proteins, OspG, OspF and IpaH were tested for phosphatase activity. Purified OspF directly dephosphorylated Erk2 (FIG. 2B). Antibodies that detect either the phospho-Thr$^{183}$ (pT$^{183}$) orphospho-Tyr$^{185}$ (pY$^{185}$) residues located at the TEY sequence of the activation loop domain were used to detect specific dephosphorylation at those residues in Erk. OspF dephosphorylated both Thr and Tyr residues (FIG. 2C, lane 2). Therefore, OspF was a dual specific phosphatase. Its phosphatase activity was inhibited by the tyrosine phosphatase inhibitor vanadate (FIG. 2C lane 3) but not by the serine threonine phosphatase inhibitor okadaic acid (FIG. 2C lane 4).

To determine the kinetic parameters of OspF-catalyzed dephosphorlylation, recombinant Erk2 was $^{33}$P-labeled by in vitro phoyphorylation using the kinase MEK1 (FIG. 2D, lane 1) and generation of Erk2 phosphorylated on pT$^{183}$ or pY$^{185}$ residues was verified with the phospho-specific Erk2 antibody (FIG. 2E, lane 1). The substrate was incubated with OspF or the known dual specific phosphatase MKP1, as a control. Dephosphorylation of Erk2 by both enzymes was confirmed by the gel-mobility increase of the substrate revealed in SDS-PAGE/autoradiography and Western blotting, with a strong inhibition of the phopho-Erk signal (FIGS. 2D and 2E, compare lane 1 to lanes 2 and 3).

The kinetic parameters were determined by following the production of radioactive inorganic phosphate. FIG. 2F shows a typical set of initial velocities versus recombinant pErk2 concentration at pH 8 and 30° C., compared to MPK1. Direct curve-fitting of the data to the Michaelis-Menten equation yielded a $V_{max}$, $K_m$, and $k_{cat}$ of 9.89 pM s$^{-1}$, 204 nM, and 0.0001 s$^{-1}$, respectively. These values were similar to the values observed with MKP1 ($V_{max}$, $K_m$, and $k_{cat}$ of 6.01 pM s$^{-1}$, 229 nM, and 0.0006 s$^{-1}$, respectively). Therefore, the kinetic parameters for the OspF-catalyzed dephosphorylation of Erk2 are comparable with the valued obtained with the mammalian DSP MKP1. Remarkably, the primary amino acid sequence of the OspF does not contain the canonical catalytic active site sequence His-Cys-Xaa$_5$-Arg-(Ser/Thr) present in all DSPs (for review see Zhang, 2002). Within the canonical catalytic motif, the cysteine (cys) residue forms a covalent bond to the phosphate provided by the substrate, therefore essential for catalysis. The histidine (His) also plays a central role in the catalysis as its imidazole ring interacts with the Cys and maintains the proper position of this residue in the P-loop of the phosphatase (Kim et al., 2001).

To probe their possible implication in the catalytic site, the conserved Cys (Cys$^{88, 163, and 180}$) and His residues of OspF were mutated into serine (Ser) and leucine (Leu), respectively. Expression plasmids for each of these mutants were transfected into HeLA cells. None of the mutations of the three Cys residues of OspF into Ser (C88S, C163S, and C180S) impaired the ability of the protein to dually dephosphorylate Erk after PMA stimulation. Simiarly, the His to Leu mutation at position 172 resulted in retention of phosphatase activity (FIG. 2G, lanes 13-17). In contrast, a single point mutation of the His104 residue into Leu (H104L) impaired the ability of OspF to dephosphorylate Erk in vivo (FIG. 2G, lanes 8-12). In parallel, the H104L mutant was purified as a GST-fusion protein. This protein was unable to dephosphorylate a recombinant phospho-Erk2 substrate even at high concentrations (FIG. 2H, lanes 7-11). Taken together, these results show that OspF is not a Cys-based PTP and suggest that the activity of the phosphatase required His104.

A sequence motif of DxDGS was identified in the C-terminal domain of OspF (motif Asp$^{217}$-X-Asp$^{219}$-Gly-Ser) (SEQ ID NO. 9). This sequence resembles the DxDG(T/V) conserved motif found in aspartate-based PTP in which the first aspartate undergoes metal-assisted phosphorylation during catalysis while the second aspartate acts as a general acid (Collet et al., 1998, for review Alonso et al., 2004). This class of enzyme is inhibited by the berylloflouride anion BeF3- known to structurally mimic a phospho-aspartate intermediate (Cho et al., 2001; Kamenski et al., 2004; Yan et al., 1999). Likewise, OspF activity was inhibited by various phosphate analogs such as orthovanadate, aluminum fluoride, and beryllofluoride, suggesting the presence of a catalytic aspartate residue (FIG. 2I, lanes 4-9). But OspF acted in a metal-independent manner since its activity was not blocked by EDTA. Moreover, conservative mutation of the two aspartate residues D217 and D219 into asparagine did not impair phosphatase activity on a GST-Erk2 substrate. Therefore, the phosphatase activity of OspF relied on a novel reaction mechanism and OspF likely represents a new class of tyrosine phosphatase.

To investigate whether OspF had phosphatase activity in vivo, HeLa cells were transfected with increasing amounts of a plasmid encoding myc-labelled OspF, which resulted in a dose-dependent increase of immunodetectable protein, and stimulated by PMA (FIG. 3A) or TNF (FIGS. 3B and C). Expression of myc-labelled OspF prevented phosphorylation of both endogenous Erk (FIG. 3A) and p38 MAP kinases (FIG. 3B) but not of p46 and p54 JNK kinases (FIG. 3C).

An ospF mutant strain (ospF strain) was constructed in which inactivation of the ospF gene was obtained by insertion of a suicide plasmid carrying an internal fragment of ospF, leading to the disruption of gene expression. The ospF mutant did not exhibit any difference compared with the wild-type strain with respect to entry into epithelial cells and dissemination of intracellular bacteria from cell to cell. The ospF strain transcomplemented with ospF (ospF/pUC-OspF) was used as an internal control.

Infection of Caco 2 cells with the ospF mutant induced phosphorylation of Erk (FIG. 3D lanes 7-9) and p38 MAPKs (FIG. 3E lanes 7-11) and the phosphorylation status of p46 and p54 JNK kinases was unchanged compared to samples in which OspF was expressed (FIG. 3F). Similar results were obtained with HeLa cells. Complementation of the ospF mutant with OspF reversed this phenotype, resulting in no phosphorylation of Erk and p38 MAP kinase (FIGS. 3D and 3E). Thus, OspF displays in vivo a dual specific activity which selectively inactivates distinct MAP kinases.

The substrate specificity of OspF was further investigated by assaying phosphatase activity on purified phospho-MAP kinase proteins. OspF directly dephosphorylated both Erk and p38 MAP kinases but, in contrast to MKP1, failed to dephosphorylate JNK1 (FIG. 3G). Thus, OspF is required to inactivate a subset of MAPKs activated upon entry of bacteria.

FIG. 1E suggested that MAP kinases were dephosphorylated inside the nucleus. The intracellular distribution of OspF after bacterial challenge was investigated. Indirect immunofluorescence was performed using an anti-OspF antibody. This antibody did not crossreact with any cellular protein and strongly immunoreacted with OspF when overexpressed in cells. HeLa cells were infected with the WT *Shigella* strain or the ospF strain as a control. In these cells, OspF accumulated in the nucleus within 15 minutes of infection with WT, while no signal was observed with the ospF deficient strain (FIG. 3H). Double labeling performed with anti-OspF and anti-nuclear pore complex protein (NPC) antibodies confirmed the nuclear localization of OspF during *Shigella* infection (FIG. 3I). Thus, the nuclear localization of OspF is consistent with the nuclear accumulation of Erk in its dephosphorylated form observed after *Shigella* infection (FIG. 1E).

Example 4

OspF Phosphatase Represses Gene Transcription of Immune Genes During *Shigella* Infection in Epithelial Cells To investigate whether OspF modulates the transcriptional response induced by *Shigella* in epithelial cells, a transcriptome analysis was performed using Caco 2 cells infected for 2 hours with WT, the ospF mutant (ospF strain), or the transcomplemented strain (ospF/pUC-OspF) of *Shigella*. Two independent microarray hybridization experiments were performed for each strain. A total of 46 genes whose transcription was upregulated by a factor of more than 1.5 upon infection with the ospF strain (compared to WT) were identified (FIG. 4). Only 3 genes were upregulated upon infection with the transcomplemented strain, indicating that the upregulation observed with the mutant strain reflects the absence of expression of the OspF protein. The upregulated genes were mainly included some classical MAPK-dependent target genes that were involved in cell survival (BCL2 family members) and several Immediate-Early (IE) genes such as genes encoding early growth factors and the AP-1 proteins, and some NF-κB dependent cytokines such as CCL-20. Hierarchical clustering of modulated gene expression is shown in FIG. 4. There are a considerable number of inflammatory or cancer diseases involving an hyperactivation of Erk or p38. In chronic inflammatory diseases like rheumatoid arthritis (RA) and inflammatory bowel disease (IBD) (Waetzig, 2002), p38 mitogen-activated protein (MAP) kinase occupies a central role in the production of IL-1 beta and TNF alpha, both cytokines being clearly identified as therapeutical targets for these diseases (Miwatashi, 2005; Peifer, 2006).

For genes encoding chemokines, the absence of OspF caused *Shigella* to induce a mRNA expression pattern similar to the one induced by the WT strain but with an overall increase in the expression levels. This increase was particularly important in the case of the dendritic chemoattractant chemokine CCL20 and the IL-8 gene, indicating a role for OspF in modulating the expression of inflammatory chemokines. These findings were confirmed by RT-PCR analysis. The results showed that the ospF mutant strongly upregulated both c-fos and IL-8 mRNA expressions, as compared to the wild type strain (FIG. 5A). For these genes, upregulation at the protein level was also observed. Western blot analysis showed that accumulation of the c-fos protein strongly increased at the early time points after infection with the ospF mutant strain but not with the WT strain (FIG. 5B, compare lanes 2-3 to 6-7), the phenotype being completely reversed with the transcomplemented strain (FIG. 5B, lanes 10-13). Considering the major role of IL-8 in the pathogenesis of shigellosis (Sansonetti et al., 1999), the expression of IL-8 mRNA was monitored. IL-8 encoding mRNA was strongly upregulated with the mutant ospF strain (FIG. 5A). Likewise, the level of IL-8 section observed after 5 hours of bacterial infection was strongly enhanced in response to the ospF strain, as compared to the WT and transcomplemented strains (FIG. 5C).

Taken together, these results show that OspF represses a selective set genes mainly involved in the inflammatory and innate immune responses. By targeting the Erk1/2 and p38 signalling pathway in epithelial cells, *Shigella* can control the pro-inflammatory process in epithelial cells.

Example 5

OspF Phosphatase Impairs Phosphorylation of Histone H3 in *Shigella*-Infected Cells Through MAPK Inactivation In addition to the classical MAPK-dependent target genes, OspF also repressed expression of some NF-κB-dependent chemokine genes such as IL-8. The IL-8 promoter contains an NF-κB binding site essential for expression of this gene (Hoffmann et al., 2002). Therefore, the inventors looked whether OspF interferes with the NF-κB signaling pathway. Electromobility shift assay (EMSA) performed with Caco 2 nuclear extracts showed that both WT and ospF strains induced a similar nuclear NF-κB binding activity detected after 1 hour of infection (FIG. 5D). Supershift analysis performed with anti-p50 and p65 antibodies indicated that both *Shigella* strains generated typical p50-p65 NF-κB dimers. (FIG. 5E). Furthermore, NF-κB transcriptional activity per se was not affected since IκB-α, a typical NF-κB dependent gene, was similarly upregulated with the WT and ospF strains, at the transcriptional level and translational level (FIG. 5F). Finally, overexpression of OspF in Caco 2 cells did not impair TNF-α-induced activation of a NF-κB reporter construct. These results showed that OspF did not impair activation of the IKK-NF-κB pathway induced by *Shigella*.

The inventors investigated how inhibition of MAPK mediated by OspF could result in repression of a selective set of NF-κB responsive genes. MAPKs are required for unpacking chromatin structures masking NF-κB binding sites on a subset of cytokine and chemokine genes, including IL-8 (Saccani et al., 2002). Indeed, covalent modifications of histones such as MAPK-induced phosphorylation of histone H3 at Ser 10 marks promoters for NF-κB recruitment (Id.). Furthermore, this histone modification has been correlated with IE genes (Clayton et al., 2000). As described above, induction of IE genes are repressed by OspF. OspF could act as a transcriptional repressor by inhibiting the major MAPKs responsible for histone H3 phosphorylation at Ser 10 (H3 pS10), namely p38 and Erk.

To test this hypothesis, HeLa cells were infected with WT *Shigella* or the ospF mutant strains and an immunofluorescence (IF) assay was performed using an anti-phospho-histone H3 Ser 10 antibody (FIG. 6A). The WT strain was unable to trigger phosphorylation of histone H3 at Ser 10 (H3 pS10) whereas the ospF strain induced a strong and transient H3 pS10 signal (FIG. 6A). Similar results were observed using Caco 2 cells. To avoid detection of mitotic H3 pS10, HeLa cells were arrested in S phase using a double thymidine block. When the cells were infected with the ospF strain, induction of phosphorylation of H3 S10 was visualized by Western blot (FIG. 6B). To verify that the absence of H3 pS10 signal upon infection by the WT strain was not due to modifications potentially masking the epitope, antibodies specific for double modifications were tested. As shown in FIG. 5B, an antibody directed against histone H3 carrying both methylated K9 and phosphorylated Ser10 (H3 metK9-pS10) and both phosphorylated Ser10 and K14 acetylated (H3pS10/Ac-K14) led to the same result as the anti-H3 pS10 antibody.

A plasmid encoding myc-labelled OspF was used to overexpress OspF in HeLa cells. Overexpression of OspF did not impair the ability of the deacetylase inhibitor trichostatin to induce hyper acetylation on K14. Immunofluorescence showed that OspF mainly localized to the nucleus and efficiently prevented induction of H3 pS10 induced by okadaic acid (FIG. 6C). Thus, variations of the levels of phosphoacetylated histone H3 are likely to reflect the sole capacity of OspF to reduce the level of phosphorylation at Ser10.

Altogether, these results showed that OspF prevented Histone H3 S10 phosphorylation during *Shigella* infection. To identify the molecular mechanism involved in this process, the inventors determined whether OspF directly dephosphorylated H3. Purified OspF was incubated with histone H3 purified from calf thymus or various peptides mimicking the histone H3 tail carrying mctK9-pS10 or pS10 modifications (FIGS. 6D and 6E). These results indicate that, in contrast to the lambda phosphatase, OspF did not directly dephosphorylate these substrates, even when the enzyme concentration was increased 100 fold. Interestingly, the H3 pS10 signal induced by the ospF strain was fully inhibited when both p38 and Erk activations were blocked by U0126 and SB 203180, two specific Erk and p38 kinase inhibitors. (FIG. 6F). This observation showed that these two kinases were responsible for the H3 pS10 observed upon infection by the ospF strain and suggested that the DSP activity mediated by OspF towards MAPKs played a central role in blocking *Shigella*-induced phosphorylation of histone H3.

The flexible N-terminal tail of histone H3 is also subject to other covalent modifications in the neighbourhood of Ser10. These modifications include Lys 14 (K14) acetylation associated to transcriptional activation, as well as Lys 9 (K9) methylation known to be a hallmark of repression. To verify that the absence of H3pS10 upon infection with the *Shigella* WT strain was not due to modifications potentially masking the epitope, antibodies specific for double modifications were tested. As shown in FIG. 6B, an antibody directed against histone H3 tails carrying both methylation on K9 and phosphorylation on Ser 10 (H3 metK9-pS10) or carrying both Ser 10 phosphorylation and Lys 14 acetylation (H3pS10/Ac-K14) led to the same result as the anti-phospho-histone H3 Ser 10 antibody.

These results confirmed that OspF impaired *Shigella*-induced phosphorylation of histone H3 S10. It also indicates that OspF prevented the formation of phosphoacetylated histone H3 at Ser10-K14. However, variations of the levels of phosphoacetylated histone H3 are likely to reflect the capacity of OspF to reduce the level of phosphorylation at Ser 10 since overexpressing OspF did not impair the ability of the deacetylase inhibitor trichostatin to induce hyper acetylation on K14 (FIG. 6G). These results showed that OspF selectively targeted histone H3 at Ser 10.

Example 6

OspF Inhibits Formation of Histone H3 Phosphorylated Promoters in a Gene-Selective Manner and Impairs Recruitment of Both NF-κB and RNA Polymerase II at the IL8 Promoter Site To investigate whether OspF altered phosphorylation of histones H3 in the vicinity of the IL-8 promoter, chromatin immunoprecipitation (ChIP) assays were performed with anti-H3 metK9-pS10 antibody or irrelevant IgG of the same isotype as a control. The average size of sonicated chromatin was approximately 500 bp, allowing analysis of the PCR products (150 bp) (FIG. 7A) and data were analyzed by Real-Time quantitative PCR.

As controls, the CD44 gene and the gene encoding ribosomal protein large P0 (RLP0) were used. These genes were well transcribed in Caco 2 cells but independently of Erk or p38 MAPKs signalling pathways. RT-PCR analysis showed that the levels of CD44 mRNA expression remained unchanged upon infection with the WT and ospF strains (FIG. 5A). The inventors also examined the gene encoding for the ribosomal protein large P0 (RLP0). RT-PCR analysis indicated that bacterial challenges upregulated RLP0 mRNA expression in an OspF-independent manner, providing an interesting positive control for these experiments (FIG. 5A). As a typical member of the NF-κB responsive genes not repressed by OspF, the IκB-α gene was examined. This gene was previously reported to undergo H3 phosphorylation in a MAPK-independent manner in dendritic cells (Saccani et al., 2002). As mentioned above, this gene was similarly upregulated by the WT and ospF strains both at the transcriptional and translational levels (FIG. 5F).

Figure 7:
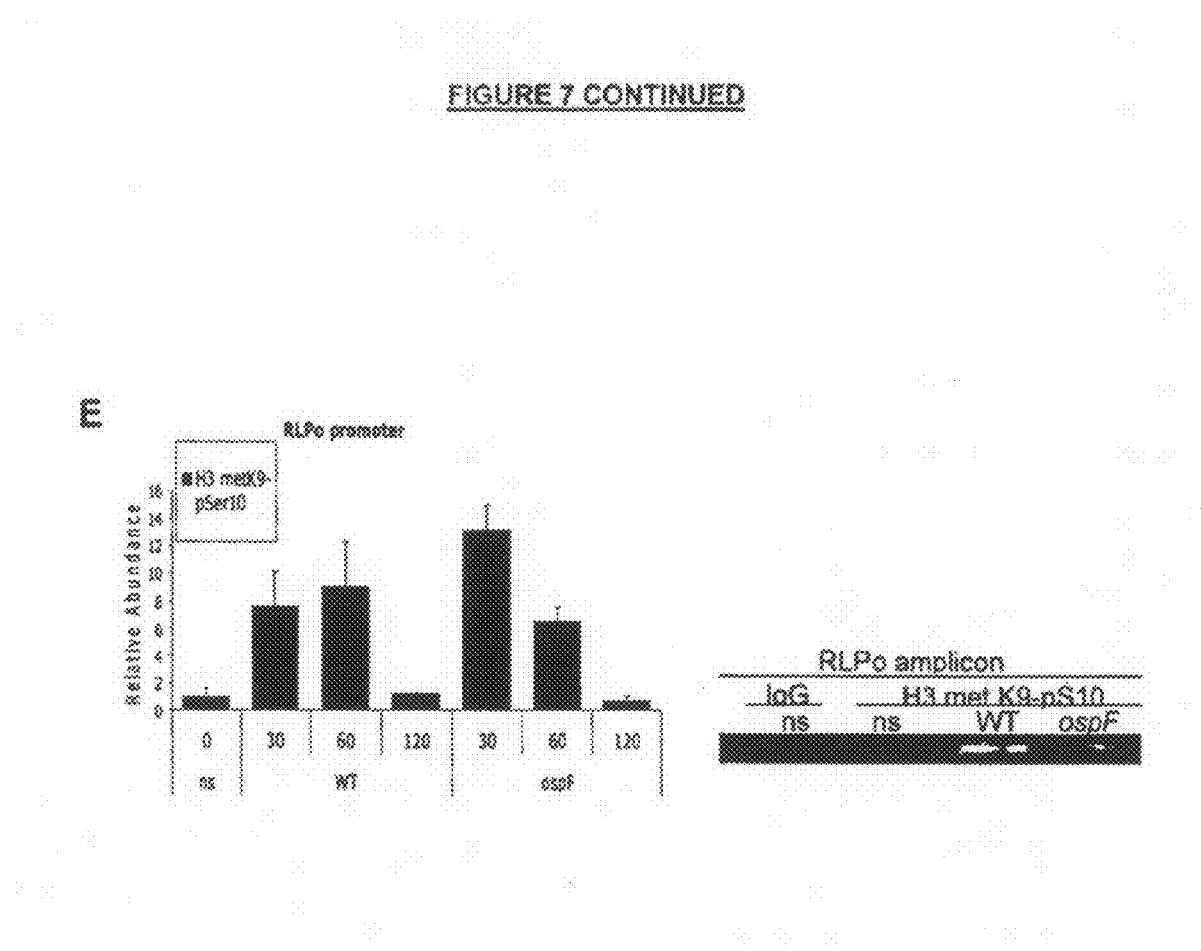
FIG. 7 shows that OspF selectively impairs Histone H3 phosphorylation and the recruitment of NF-κB at the IL-8 promoter. (A) DNA isolated from sonicated cross-linked chromatin fragments used as inputs for ChIp assays run on a 2% agarose/TAE gel. (B) Cross-linked chromatin fragments were prepared from Caco 2 cells left untreated (ns) or infected with the WT or the ospF strains at the indicated time. For each time point, aliquots were immunoprecipitated with irrelevant IgG, anti-H3 methyl K9-pS10, or anti-p65 antibodies. Histograms show the results obtained by Real-Time PCR analysis using amplicon from the promoter region of IL-8. Data are expressed as relative enrichment as compared to the result obtained with the corresponding IgG that have been immunoprecipitated at the same time point. The lower panel shows the agarose gel electrophoresis of the PCR products obtained after 1 hour bacterial challenge. (C) The data are given as in figure (B) except that the aliquots were immunoprecipitated with irrelevant IgG or anti-RNAPII antibodies. The right panel shows the PCR products obtained after 1 hour bacterial challenge. (D, E, F) The aliquots were immunoprecipitated with irrelevant IgG or anti-H3 methyl K9-pS10 antibodies. Histograms show the results obtained by real-time PCR analysis using amplicon from the promoter region of the CD44 (D), RLP0 (E) or the IκB-α (F) genes. The right panel shows the PCR products obtained 1 hour after bacterial challenge. (G) Indirect immunofluoescence detection of OspF mutants. HeLa cells were transfected with pRK5 myc-ospF, ospF (H104L), or ospF (1-221). IF was performed with an anti-OspF antibody. (H) HeLa cells were transfected with pRK5 myc-WT ospF, ospF H104L, ospF (1-221) and stimulated by TNF-α at the indicated times. The aliquots were immunoprecipitated with irrelevant IgG or anti-OspF antibodies. Histograms show the results obtained by real time PCR analysis amplifying an amplicon from the promoter region of the IL-8, CD44, RLP0 and IκB-α genes.

Consistent with the data obtained by IF and Western Blot (FIGS. 6A and 6B), infection of Caco 2 cells with the ospF strain resulted in an approximately 400 fold increase in the level of histone H3 phosphorylation at Ser10 (H3pS10) on the IL-8 promoter within 30 minutes of infection, whereas the WT strain had almost no effect (FIG. 7B, left panel). Therefore, OspF strongly repressed formation of H3pS10 at the IL-8 promoter. Interestingly, OspF did not modify H3 phosphorylation on the CD44 and IκB-α amplicons (FIGS. 7D and 7F). Furthermore, the presence of OspF never affected the robust recruitment induced by both bacterial challenges of phosphorylated histone H3 that contact the RLP0 promoter (FIG. 7E). These results indicated that the effect of OspF on histone H3 was gene specific.

It is possible that this gene specificity could be more easily achieved by a direct spatial localization of the bacterial effector at the target promoter. To explore this possibility, HeLa cells were transfected with a plasmids encoding WT OspF, catalytically inactive OspF H104L or, as a control, a C-terminal deletion mutant of the last 30 amino acids of OspF (1-221), which cannot localize to the nucleus (FIG. 7G). These HeLa cells were processed for ChIP assay using the anti-OspF antibody.

Recent evidence in both yeast and human systems indicates that, once activated, MAPK localizes within the nucleus to stably associate with the chromatin that harbors their target genes (Alepuz, 2001, Pokholok, 2006), opening up the possibility that the kinase activity could initiate signaling pathways leading to gene-specific modifications at the chromatin level. Since OspF acted as a phosphatase dephosphorylating MAPKs within the nucleus, cell activation could target OspF at the selected promoter to interrupt the MAP kinase signaling cascade leading to H3 phosphorylation.

To address whether MAPK-induced H3pS10 in the vicinity of the IL-8 promoter, HeLa cells expressing the plasmids encoding WT ospF, or as control, a C-terminal deletion mutant of the last 30 amino acids ospF (1-221) unable to localize within the nucleus (FIG. 7G) were processed for chromatin immunoprecipitation (ChIP) assay using the anti-OspF antibody and the enrichment of OspF at the IL-8 promoter was analyzed by Real-Time quantitative PCR. As additional controls, various genes not repressed by OspF were also examined in this transcriptional analysis: IκB-α, CD44 and the gene encoding the ribosomal protein large P0 (RLP0) which was transcriptionally induced by Shigella challenge in an OspF-independent manner (FIG. 5A).

Whereas immunofluorescence indicated a strong accumulation of OspF within the nucleus (FIG. 7G), OspF was not detectable at the IL-8 promoter in unstimulated cells (FIG. 7H). By contrast, TNF-α stimulation induced a transient recruitment of OspF at the IL-8 but not at the IκB-α, RLP0 or CD44 promoters. In unstimulated cells, no signal was detected at the IL-8 promoter (FIG. 7H). This result suggested that inflammatory stimuli could potentially drive this effector at the selected promoter, providing an attractive mechanism for inducing site-specific down-regulation of MAPK-induced H3 S10 phosphorylation at the level of the promoters. Thus, cell stimulation targets OspF at the selected promoter, providing an attractive mechanism for inducing site-specific epigenetic modifications to particular loci.

A model was proposed suggesting that H3 phosphorylation by MAPK kinase activation was a prerequisite for unmasking the NF-κB binding sites on particular genes (Muegge, 2002). This model was mainly supported by the fact that treatment of the cells by pharmacological MAPK inhibitors decreased the recruitment of the p65 NF-κB subunit to the IL-8 promoter (Saccani et al., 2002). The highly selective DSP activity of OspF towards p38 and Erk allowed direct assessment of their role in this process.

ChIP assays using an antibody directed against the p65 subunit of NF-κB were performed. The CD44 amplicon was used as a negative control since this gene does not contain any NF-κB binding site. As shown in FIG. 7B (right panel), inactivation of ospF considerably facilitated p65 recruitment to the IL-8 promoter induced by Shigella whereas no signal could be detected at the CD44 promoter. As the p65 subunit activated transcription by recruiting RNAPII (Xia et al., 2004), a ChIP assay was performed with an antibody immunoprecipitating the total pool of RNA polymerase II. As expected, the experiment showed an increased binding of RNA polymerase II to the IL-8 promoter in the absence of OspF (FIG. 7C). Thus, OspF altered the recruitment of major transcriptional components at the selected promoter.

Example 7

OspF Phosphatase Inhibits IL-12 Production

The cytokine/chemokine network induced upon infection with *Shigella flexneri* was analyzed by comparing the profiles obtained upon infection with the invasive strain carrying the virulence plasmid (INV+) and the non-invasive, plasmidless strain (INV−). The murine model of pulmonary infection was used since it was the only valid model to analyze the specific host immune response upon Shigella infection. Following infection with INV−, a Th1 type-network (IL-12, IL-18, IFN-γ, CCL9, CCL10, CCL13, and CCL4) was induced. In contrast, a Th2/Tr1 profile (IL-10, CCL1, CCL24 and CCL2) was induced upon infection with INV+. The difference observed was not due to the bacterial dose used for the infection, but was dependent on the presence or absence of the virulence plasmid. These results showed that invasive Shigella inhibited the production of IL-12/IFN-γ.

The dendritic cells (DC), which are one of the major sources of IL-12, were targeted by Shigella at the early time point post-infection. In fact, DCs recovered from INV+-infected mice did not produce IL-12 whereas DCs recovered from INV-infected mice do (FIG. 8). The assumption was that the bacterium, to establish its infectious process, created a favourable local environment deprived of IFN-γ, which was required for the eradication of the primary infection, and thus, deleterious for Shigella. (Le Barillec K., et al.). In contrast to other infectious models (McGuirk, 2002 and Sing, 2002), in IL-10 knocked-out (KO) mice this cytokine did not play a central role in the inhibition of IL-12/IFN-γ pathway, since the production of these cytokines was still inhibited in INV+-infected IL-10 KO mice (FIG. 9). This result suggested that one or more virulence factors are involved in this inhibition.

Some of these bacterial effectors are injected within the host cells by a type III secretion apparatus. Use of different bacterial mutants, has highlighted that the bacterial effectors involved in the immunomodulation were effectors secreted by the type III-secretion apparatus. Finally, OspF, a type III-secreted bacterial effector was responsible fore the control of IL-12 production (FIG. 10).

Example 8

Effect of OspF Phosphatase on Development of Protective Immune Response

The impact of the immunomodulation associated with *Shigella* infection on the induction of the adaptive immunity was studied. Three groups were analyzed. The first group was infected with the M90T strain, the second group was infected with the ospF strain, and the third group was infected with water (control group). Mice were vaccinated with $10^8$ bacteria per mouse and 3 weeks later the mice were boosted with $10^7$ bacteria per mouse. Eight weeks after boosting, the mice were challenged with a lethal dose of bacteria ($5 \times 10^8$ bacteria per mouse) and were monitored for survival. As shown in FIG. 11, mice vaccinated with the OspF mutant were more efficiently protected against challenge than mice vaccinated with INV+.

Example 9

OspF is a Repressor of Polymorphonuclear Leukocyte Recruitment In Vivo

OspF affects expression of a subset of immune genes. Therefore, the in vivo relevance of this regulation was investigated by using the rabbit ligated ileal loop model of infection. The rabbit intestinal loops were infected for 8 hours with the WT strain, the ospF mutant, or the transcomplemented strain (ospF/pUC-OspF) as a control. Haematoxylin staining indicated that, compared to the WT strain, the ospF mutant caused more severe mucosal lesions, increased shortening and enlargement of the villi, and more extended areas of epithelial destruction generally corresponding to abscesses. The complemented mutant restored a phenotype similar to that of the WT strain.

Figure 14:
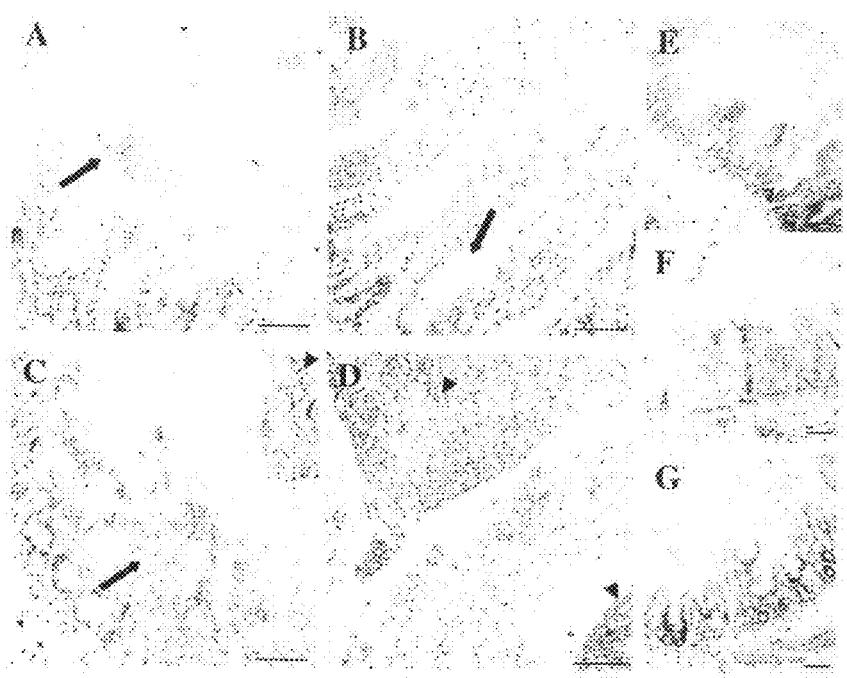
FIG. 14 shows that OspF represses polymorphonuclear leukocyte recruitment and restricts bacterial invation of intestinal epithelium. Histopathological sections of rabbit ligated ileal loops that were infected for 8 hours with the WT strain (A, E), the ospF mutant strain (B, C, F), or the transcomplemented mutant strain (B,G). In (A-D), anti-LPS immunostaining was performed as described in Example 1. In (A, B) arrowheads show localized epithelial abscesses similar common to the WT and transcomplement strains. In (C, D) arrowheads define areas of extensive diffusion of bacteria in the subepithelial lamina propria and massive accumulation of inflammatory cells in the lumen following infection with the ospF mutant strain. (E-F) Anti-NP5 immunostaining was performed, confirming the extensive PMN infiltration of the lamina propria and the massive translocation of PMNs is not in the intestinal lumen in loops infected with the ospF mutant strain (F), compared to the limited infiltration observed with the WT and ospF transcomplemented with puc-OspF (E, G). Bars equal 10 μm.

For immunolabeling experiments, bacteria were stained with an anti-S. flexneri 5a LPS antiserum (FIGS. 14A-D), and polymorphonuclear leukocytes (PMNs) with an anti-NP5 antiserum (FIGS. 14E-G), this antimicrobial peptide being strongly expressed in these cells. LPS staining indicated that the WT bacterial remained essentially localized to epithelial and immediately sub-epithelial zones, in abscesses. These abscesses disrupted the epithelial lining and were often localized at the bottom of a deep indentation formed in the villus structure (FIG. 14A). In addition, a limited efflux of migrating inflammatory cells was often seen, streaming from these ulcerated lesions (see arrow, FIG. 14A). NP5 staining confirmed the presence of PMN in these infected areas and showed some level of PMN infiltration in the lamina propria, oedematous sub-mucosal tissues, and in the lumina (FIG. 14E).

Anti-LPS staining of tissues infected by the ospF mutant showed a dramatically different pattern of infection characterized by a massive bacterial infiltrate in the lamina propria, far beyond the superficial ulcers associated with WT infection (see arrow, FIG. 14C). In parallel, massive luminal efflux of inflammatory cells was observed, many of them associated with bacteria (see arrowhead, FIG. 14D). NP5 staining confirmed extensive PMN infiltration of the lamina propria and their massive efflux into the intestinal lumen (FIG. 14F). Both stainings indicated that the transcomplemented mutant had recovered a wild type phenotype (FIG. 14B, arrowhead and 14G). In sum, these experiments indicated that OspF was a major negative regulator of PMN recruitment in Shigella-infected tissues.

CONCLUSIONS

Gram-negative animal and plant pathogens use specialized secretion systems to translocate effector proteins into host cells. A few of these effectors are tyrosine phosphatases: YopH from Yersinia pseudotuberculosis suppresses actin polymerization (Andersson et al., 1996), SptP from Salmonella typhimurium disrupts the actin skeleton (Fu and Galan, 1998), and HopPtoD2 from Pseudomonas syringae is a programmed cell death suppressor in plants (Espinosa et al., 2003). In general, these effectors display a high degree of selectivity for phospho-Tyr residues (Kennelly, 2001), with the exception of the IphP protein form the non-pathogenic cyanobacterium Nostoc commune that hydrolyzes both phospho-Ser and phospho-Tyr residues in vitro (Potts et al., 1993). IphP is chromosome-encoded and probably located in the periplasm. It shares structural similarities with mammalian DSPs, but its function is as yet unknown (Id.). In contrast, OspF is encoded by the 220 kb virulence plasmid that encodes the invasive phenotype of Shigella. OspF is translocated into target eukaryotic cells and is characterized here as the first DSP involved in bacterial virulence.

Interestingly, OspF does not contain the canonical catalytic active sequence His-Cys-Xaa$_5$-Arg-(Ser/Thr) present in all other DSPs, arguing against an eukaryotic origin for this protein. However, the striking sequence homology of OspF with putative virulence proteins from other proteobacteria (FIG. 13) suggests the existence of a common ancestor, acquired and maintained as a selective advantage for these bacteria. To date, four classes of protein tyrosine phosphatases (PTP) have been identified, based on the amino acid sequences of their catalytic domain (for review see Alonso et al., 2004). Three of these groups are cysteine-based PTPs and include the tyrosine specific conventional PTPs such as YopH, SptP, HopPtoD2 and the DSPs. OspF is not a member of these classes as we have mutated all its cysteine residues and found no effect on the catalytic activity.

A fourth class defines aspartate-based PTPs including the RNA polymerase II CTD phosphatase and the transcriptional regulators from the Eyes absent family (for review see Rebay et al., 2005). These PTPs share a conserved DxDG(T/V) catalytic motif, are strictly magnesium dependent, and are inhibited by beryllium chloride (Cho et al., 2001 and Kamenski et al., 2004). The OspF activity was also inhibited by beryllium chloride, suggesting the presence of a catalytic aspartate residue. Moreover, OspF contains a sequence resembling a DxDG(T/V) motif. The catalytic activity, however, could not be assigned to this sequence. Taken together, these observations suggest that OspF is not a classical aspartate-based PTP and may define a new class of tryosine phosphatases.

OspF is very selective for inactivation of the Erk and p38 MAP kinases and transcriptional analysis indicates that it represses the expression of a narrow, though essential, set of genes encompassing the IE genes and some NF-κB responsive genes like IL-8. This is reflected by in vivo experiments showing that, compared to wild type Shigella, the ospF mutant generated overwhelming mucosal infiltration by PMNs and massive subsequent transepithelial migration into the gut lumen. Ample evidence indicates that IL-8 is the major effector of PMN mucosal trafficking in the course of experimental Shigella infection (Sansonetti et al., 1999), and that the lack of intestinal inflammation in mice infected by Shigella is largely due to the absence of this chemokine in the murine lineage (Singer and Sansonetti, 2004). It is most likely that injected effectors such as OspF are dedicated to very focused, but essential physiological functions, the additive effect of each of the injected effectors such as OspF, OspG (Kim et al., 2005), and eventually others, leading to the very specific tuning of the host transcriptional innate response.

The restricted range of promoters stimulated upon OspF inactivation implied that this bacterial effector does not control all genes potentially activated by the MAPK pathway. This was not unexpected as inducible promoters can, in most cases, respond to additional signal transduction pathways activated by pro-inflammatory stimuli. However, the specificity of OspF raises the question of how this bacterial phosphatase can secure repression of a selective set of target genes and more specifically a subset of NF-κB responsive genes. The existence of specific chromatin configurations that are non permissive for NF-κB recruitment was recently invoked to explain how NF-κB is kept from binding to several NF-κB responsive genes like IL-8 (for review see Natoli et al., 2005). For these genes, MAPK-dependent histone modification such as H3 phosphorylation at Ser10 promotes chromatin decompaction at the promoter site, thereby permitting successful recruitment of NF-κB (Muegge, 2002; Saccani et al., 2002). The inventors investigated the functional effect of OspF on the phosphorylation status of histone H3 and found that OspF prevented histone H3 phosphorylation at Ser10. This effect was not randomly distributed but rather gene-specific. Such a level of regulation could be more easily achieved by a direct spatial localization of the bacterial effector a the selected target promoter. Chromatin immunoprecipitation showed that cell stimulation by pro-inflammatory stimuli like TNF-α induced the direct localization of this effector at the selected promoter.

The presence of OspF at the promoter site is consistent with earlier studies on yeast and humans showing that the MAPK p38 is directly recruited to target promoters where it initiates a signaling pathway that led to site-specific modifications impacting transcription (Alepuz et al., 2001; Simone et al., 2004; Edmunds and Mahedevan, 2004). Gene recruitment of OspG may induce MAPKs dephosphorylation within the nucleus at the relevant promoter sites, inactivating a protein kinase cascade that leads to localized H3 phosphorylation. Examination of several promoters revealed that inappropriate H3 Ser10 phosphorylation was observed only at genes regulated by OspF. Taken together, these observations suggest that one important mechanism for the selective transcriptional control mediated by OspF is a site-specific down regulation of MAPK-induced H3 Ser10 phosphorylation at the level of the promoters. Evidently, it is possible OspF may also have other local targets such as promoter-bound transcription factors. In this regard, the catalytically inactive OspF mutant was more stably associated with the IL-8 promoter (at least 2 hours) than WT OspF, suggesting that OspF may target its own nuclear anchor and lead to the destabilization of its own tethering at the promoter site.

Modulation of the innate immune response, particularly inflammation, at mucosal surfaces by pathogens at the early stage of infection is a crucial requisite for both the establishment of the infectious process and the nature of the adaptive immunity that is subsequently induced. The results herein indicate that OspF induces the precise epigenetic modifications required to regulate a specific pool of genes, particularly IL-8, that controls the flow of inflammatory cells, such as PMNs, through the lamina propria and the epithelial lining of the gut. OspF also downregulates other important genes such as CCL-20, which functions as an antibacterial peptide (Hoover et al., 2002) and as a chemoattractant of immune cells (Dieu et al., 1998). In doing so, OspF may improve the survival of invading *Shigella* and dampen the adaptive immune response by blocking recruitment of dendritic cells to the site of infection. The above hypotheses, however, do not account for the paradoxical observation that the OspF mutant showed more extensive dissemination throughout subepithelial tissues (i.e., lamina propria) than the WT *Shigella*. Given this observation, the course of *Shigella* infection in the gut mucosa, as demonstrated by in vitro and in vivo models (Perdomo et al., 1994a; Perdomo et al., 1994b), the flow of PMNs migrating towards the intestinal lumen accounts for rupture of the epithelial barrier, facilitating the bacterias' access to the sub-epithelial tissues. In the case of the OspF mutant, it is clear that excessive migration should increase mucosal invation, compared to the WT strain.

In its need to regulate the host immune response, *Shigella* has chosen specific strikes, attacking the host's immune system with surgical precision. Such an approach supposes highly sophisticated strategies such as OspF reprogramming the transcriptional response through gene-specific epigenetic modifications required for inactivation of an essential set of immune genes. This adaptation is an example of the refined nature of the interaction of microbial pathogens and their hosts.

REFERENCES

The entire disclosures of each of the following publications are relied upon and incorporated by reference herein:

Alepuz, P. M., Jovanovic, A., Reiser, V., and Ammerer, G. "Stress-induced Map Kinase Hog1 is Part of Transcription Activation Complexes." *Mol. Cell* 7:767-77 (2001).

Andersson, K., Carballeira, N., Magnusson, K. E., Persson, C., Stendahl, O., Wolf-Watz, H., and Fallman, M. "YopH of *Yersinia pseudotuberculosis* Interrupts Early Phosphotyrosine Signalling Associated with Phagocytosis." *Mol. Microbiol.* 20:1057-69 (1996).

Ardizzone, S. and Bianchi Porro, G. "Biologic Therapy for Inflammatory Bowel Disease." *Drugs* 65 2253-86 (2005).

Ashida, R., Tominaga, K., Sasaki, E., Watanabe, T., Fujiwara, Y., Oshitani, N., Higuchi, K., Mitsuyama, S., Iwao, H., and Arakawa, T. "AP-1 and Colorectal Cancer." *Inflammopharm.* 13:113-25 (2005).

Axtell, M. J., and Staskawicz, B. J. "Initiation of RPS2-specified Disease Resistance in *Arabidopsis* is Coupled to the AvrRpt2-directed Elimination of RIN4." *Cell* 112:369-77 (2003).

Bai, M., Papoudou-Bai, A., Horianopoulos, N., Grepi, C., Agnantis, N. J., and Kanavaros, P. "Expression of Bcl2 Family Proteins and Active Caspase 3 in Classical Hodgkin's lymphomas." *Hum. Path. Aug.* 31 (2006).

Brondello, J. M., Brunet, A., Pouyssegur, J., and McKenzie, F. R. "The Dual Specificity Mitogen-activated Protein Kinase Phosphatase-1 and -2 are Induced by the p42/p44MAPK Cascade." *J. Biol. Chem.* 272:1368-76 (1997).

Buchrieser, C., Glaser, P., Rusnlok, C., et al. "The Virulence Plasmid pWR100 and the Repertoire of Proteins Secreted by the Type III Secretion Apparatus of *Shigella flexneri*." *Mol. Microbiol.* 38:760-71 (2000).

Burack, W. R., and Shaw, A. S. "Live Cell Imaging of ERK and MEK: Simple Binding Equilibrium Explains the Regulated Nucleocytoplasmic Distribution of ERK." *J. Biol. Chem.* 280:3832-37 (2005).

Cheung, P., Allis, C. D., and Sassone-Corsi, P. "Signaling to Chromatin Through Histone Modifications." *Cell* 103:263-71 (2000).

Cho, H. et al., "BeF(3)(−) Acts as a Phosphate Analog in Proteins Phosphorylated on Aspartate: Structure of a BcF(3)(−) Complex with Phosphoserine Phosphatase." *PNAS-USA* 98:8525-30 (2001).

Clayton, A. L., Rose, S., Barratt, M. J., and Mahadevan, L. C. "Phosphoacetylation of Histone H3 on c-fos- and c-jun-associated Nucleosomes upon Gene Activation." *EMBO. J.* 19:3714-26 (2000).

Clayton, A. L. and Mahadevan, L. C. "MAP Kinase-Mediated Phosphoacetylation of Histone H3 and Inducible Gene Regulation." *FEBS Lett.* 546:51-58 (2003).

Cornelis, G. R. "The *Yersinia* Ysc-Yop 'type III' Weaponry." *Nat. Rev. Mol. Cell Biol.* 3:742-52 (2002).

Dieu, M. C. et al. "Selective Recruitment of Immature and Mature Dendritic Cells by Distinct Chemokines Expressed in Different Anatomic Sites." *J. Exp. Med.* 188:373-86 (1998).

Dyson, M. H., Thomson, S., Inagaki, M., Goto, H., Arthur, S. J., Nightingale, K., Iborra, F. J., and Mahadevan, L. C. "MAP Kinase-mediated Phosphorylation of Distinct Pools of Histone H3 at S10 or S28 via Mitogen- and Stress-activated Kinase 1/2." *J. Cell Sci.* 118:2247-59 (2005).

Edmunds, J. W. and Mahadevan, L. C. "MAP Kinases as Structural Adaptors and Enzymatic Activators in Transcription Complexes." *J. Cell Sci.* 117:3715-23 (2004).

Espinosa, A., Guo, M., Tam, V. C., Fu, Z. Q., and Alfano, J. R. "The *Pseudomonas syringae* Type III-secreted Protein HopPtoD2 Possesses Protein Tyrosine Phosphatase Activity and Suppresses Programmed Cell Death in Plants." *Mol. Microbiol.* 49:377-87 (2003).

Fleischer, B., Schulze-Bergkamen, H., Schuchmann, M.; Weber, A., Biesterfeld, S., Muller, M., Krammer, P. H., and Galle, P. R. "Mcl-1 is an Anti-apoptotic Factor for Human Hepatocellular Carcinoma." *Int. J. Oncol.* 28:25-32 (2006).

Fu, Y., and Galan, J. E. "The *Salmonella typhimurium* Tyrosine Phosphatase SptP is Translocated into Host Cells and Disrupts the Actin Cytoskeleton." *Mol. Microbiol.* 27:359-68 (1998).

Girardin, S. E., Boneca, I. G., Carneiro, L. A., Antignac, A., Jehanno, M., Viala, J., Tedin, K., Taha, M. K., Labigne, A., Zahringer, U., et al. "Nod1 Detects a Unique Muropeptide from Gram-negative Bacterial Peptidoglycan." *Science* 300:1584-87 (2003).

Harper, J. V. "Synchronization of Cell Populations in G1/S and G2/M Phases of the Cell Cycle." *Methods Mol. Biol.* 296:157-66 (2005).

Hoffmann, E., Dittrich-Breiholz, O., Holtmann, H., and Kracht, M. "Multiple Control of Interleukin-8 Gene Expression." *J. Leukoc. Biol.* 72:847-55 (2002).

Hoover, D. M. et al. "The Structure of Human Macrophage Inflammatory Protein-3 alpha/CCL20. Linking Antimicrobial and CC Chemokine Recpetor 6 Binding Activities with Human Beta-Defensins." *J. Biol. Chem.* 277:37647-54 (2002).

Janeway, C. A., Jr., and R. Medzhitov. "Innate Immune Recognition." *Ann. Rev. Immunol.* 20:197-216 (2002).

Jenuwein, T. and Allis, C. D. "Translating the Histone Code." *Science* 293:1074-79 (2001).

Jung, H. C., Eckmann, L., Yang, S. K., Panja, A., Fierer, J., Morzycka-Wroblewska, E., and Kagnoff, M. F. "A Distinct Array of Proinflammatory Cytokines is Expressed in Human Colon Epithelial Cells in Response to Bacterial Invasion." *J. Clin. Invest.* 95:55-65 (1995).

Kamenski, T. et al. "Structure and Mechanism of RNA Polymerase III CTD Phosphatases." *Mol. Cell* 15:399-407 (2004).

Kaser, A., Ludwiczek, O., Holzmann, S., Moschen, A. R., Weiss, G., Enrich, B., Graziadei, I., Dunzendorfer, S., Wiedermann, C. J., Murzl, E., Grasi, E., Jasarevic, Z., Romani, N., Offner, F. A., and Tilg, H. "Increased Expression of CCL20 in Human Inflammatory Bowel Disease." *J. Clin. Immunol.* 24:74-85 (2004).

Kennelly, P. J. "Protein Phosphatases—a Phylogenetic Perspective." *Chem. Rev.* 101:2291-2312 (2001).

Kim D. et al. "The *Shigella flexneri* Effector OspG Interferes with Innate Immune Responses by Targeting Ubiquitin-Conjugating Enzymes." *PNAS-USA* 102:14046-51 (2005).

Kim, J. H. et al. "Mutational and Kinetic Evaluation of Conserved His-123 in Dual Specificity Protein-tyrosine Phosphatase Vaccinia H1-Related Phosphatase: Participation of Tyr-78 and Thr-73 Residues in Tuning the Orientation of His-123.". *J. Biol. Chem.* (2001).

Kubori, T., and Galan, J. E. "Temporal Regulation of *Salmonella* Virulence Effector Function by Proteasome-dependent Protein Degradation." *Cell* 115:333-42 (2003).

Le Barillec, K., Gamelas, J., Magalhaes, A. Thuizat, M. Huerre, P. J. Sansonetti, J. P. Di Santo, and A. Phalipon. "T cells are Involved in the Recovery of Primary Infection with *Shigella flexneri*." Manuscript in press in *J. Immunology*.

Lee, H. J., Choi, S. C., Lee, M. H., Oh, H. M., Choi, E. Y., Choi, E. J., Yun, K. J., Seo, G. S., Kim, S. W., Lee, J. G., Han, W. C., Park, K. I., and Jun, C. D. "Increased Expression of MIP-3alpha/CCL20 in Peripheral Blood Mononuclear Cells from Patients with Ulcerative Colitis and its Down-Regulation by Sulfasalazine and Glucocorticoid Treatment." *Inflamm. Bowel Dis.* 11:1070-79 (2005).

Li, C., and Wong, W. H. "Model-based Analysis of Oligonucleotide Arrays: Expression Index Computation and Outlier Detection." *PNAS-USA* 98:31-36 (2001).

Mackay, C. R. "Chemokines: Immunology's High Impact Factors." *Nat. Immunol.* 2:95-101 (2001).

Mateescu, B., England, P., Halgand, F., Yaniv, M., and Muchardt, C. "Tethering of HP1 Proteins to Chromatin is Relieved by Phosphoacetylation of Histone H3." *EMBO Rep.* 5:490-96 (2004).

Mavris, M., Page, A. L., Tournebize, R., Demers, B., Sansonetti, P., and Parsot, C. "Regulation of Transcription by the Activity of the *Shigella flexneri* Type III Secretion Apparatus." *Mol. Microbiol.* 43:1543-53 (2002a).

Mavris, M., Sansonetti, P. J., and Parsot, C. "Identification of the Cis-acting Site Involved in Activation of Promoters Regulated by Activity of the Type III Secretion Apparatus in *Shigella flexneri*." *J. Bacteriol.* 184:6751-59 (2002b).

McGuirk, P., C. McCann, and K. H. Mills. "Pathogen-specific T Regulatory 1 Cells Induced in the Respiratory Tract by a Bacterial Molecule that Stimulates Interleukin 10 Production by Dendritic Cells: a Novel Strategy for Evasion of Protective T Helper Type 1 Responses by *Bordetella pertussis*." *J. Exp. Med.* 195:221-31 (2002).

Menard, R., Sansonetti, P., and Parsot, C. "The Secretion of the *Shigella flexneri* Ipa Invasins is Activated by Epithelial Cells and Controlled by IpaB and IpaD." *EMBO J.* 13:5293-302 (1994a).

Menard, R. et al. "Extracellular Association and Cytoplasmic Partitioning of the IpaB and IpaC Invasins of *S. flexneri*." *Cell* 79:515-25 (1994b).

Miwatashi, S., Arikawa, Y., Kotani, E., Miyamoto, M., Naruo, K., Kimura, H., Tanaka, T., Asahi, S., and Ohkawa, S. "Novel Inhibitor of p38 MAP Kinase as an Anti-TNF-alpha Drug: Discovery of N-[4-[2ethyl-4-(3-methylphenyl)-1,3-thiazol-5-yl]-2-pyridyl]benzamide (TAK-715) as a Potent and Orally Active Anti-rheumatoid Arthritis Agent." *J. Med. Chem.* 48:5966-79 (2005).

Muegge, K. "Preparing the Target for the Bullet." *Nat. Immuno.* 3:16-17 (2002).

Mukherjee, S., Keitany, G., Li, Y., Wang, Y., Ball, H. L., Goldsmith, E. J., and Orth, K. "*Yersinia* YopJ Acetylates and Inhibits Kinase Activation by Blocking Phosphorylation." *Science* 312:1211-14 (2006).

Nhieu, G. T., and P. J. Sansonetti. "Mechanism of *Shigella* Entry into Epithelial Cells." *Curr. Opin. Microbiol.* 2:51-55 (1999).

Nielsen, O. H., Rudiger, N., Gaustadnes, M., and Horn, T. "Intestinal interleukin-8 concentration and gene expression in inflammatory bowel disease." *Scand. J. Gastroenterol.* 32:1028-34 (1997).

Numberger, T., Brunner, F., Kemmerling, B., and Piater, L. "Innate Immunity in Plants and Animals: Striking Similarities and Obvious Differences." *Immunol. Rev.* 198:249-66 (2004).

Orth, K., Xu, Z., Mudgett, M. B., Bao, Z. Q., Palmer, L. E., Bliska, J. B., Mangel, W. F., Staskawicz, B., and Dixon, J.

E. "Disruption of Signaling by *Yersinia* Effector YopJ, a Ubiquitin-like Protein Protease." *Science* 290:1594-97 (2000).

Parsot, C. "*Shigella flexneri*: Genetics of Entry and Intercellular Dissemination in Epithelial Cells." *Curr. Top. Microbiol. Immunol.* 192:217-41 (1994).

Pedron, T., Thibault, C., and Sansonetti, P. J. "The Invasive Phenotype of *Shigella flexneri* Directs a Distinct Gene Expression Pattern in the Human Intestinal Epithelial Cell Line Caco-2." *J. Biol. Chem.* 278:33878-86 (2003).

Peifer, C., Wagner, G., and Laufer, S. "New Approaches to the Treatment of Inflammatory Disorders Small Molecule Inhibitors of p38 MAP Kinase." *Curr. Top. Med. Chem.* 6:113-49 (2006).

Perdomo, J. J., Gounon, P., and Sansonetti, P. J. "Polymorphonuclear Leukocyte Transmigration Promotes Invasion of Colonic Epithelial Monolayer by *Shigella flexneri.*" *J. Clin. Invest.* 93:633-43 (1994a).

Perdomo, O. J., Cavaillon, J. M., Huerre, M., Ohayon, H., Gounon, P., and Sansonetti, P. J. "Acute Inflammation Causes Epithelial Invasion and Mucosal Destruction in Experimental Shigellosis." *J. Exp. Med.* 180:1307-19 (1994b).

Phalipon, A., and P. J. Sansonetti. "Microbial-host Interactions at Mucosal Sites. Host Response to Pathogenic Bacteria at Mucosal Sites." *Curr. Top. Microbiol. Immunol.* 236:163-89 (1999).

Phalipon, A., and P. J. Sansonetti. "Shigellosis: Innate Mechanisms of Inflammatory Destruction of the Intestinal Epithelium, Adaptive Immune Response, and Vaccine Development." *Crit. Rev. Immunol.* 23:371-401 (2003).

Philpott, D. J., Yamaoka, S., Israel., A., and Sansonetti, P. J. "Invasive *Shigella flexneri* Activates NF-kappa B through a Lipopolysaccharide-dependent Innate Intracellular Response and Leads to IL-8 Expression in Epithelial Cells." *J. Immunol.* 165:903-14 (2000).

Pokholok, D. K., Zeitlinger, J., Hannett, N. M., Reynolds, D. B., and Young, R. A. "Activated Signal Transduction kinases Frequently Occupy Target Genes." Science 313:533-36 (2006).

Potts, M., Sun, H., Mockaitis, K., Kennelly, P. J., Reed, D., and Tonks, N. K. "A Protein-Tyrosine/serine Phosphatase Encoded by the Genome of the Cyanobacterium *Nostoc commune* UTEX 584." *J. Biol. Chem.* 268:7632-35 (1993).

Saccani, S., Pantano, S., and Natoli, G. "p38-Dependent Marking of Inflammatory Genes for Increased NF-kappa B Recruitment." *Nat. Immunol.* 3:69-75 (2002).

Sansonetti, P. J., Arondel, J., Huerre, M., Harada, A., and Matsushima, K. "Interleukin-8 Controls Bacterial Transepithelial Translocation at the Cost of Epithelial Destruction in Experimental Shigellosis." *Infect. Immun.* 67:1471-80 (1999).

Schmidt, C., Giese, T., Ludwig, B., Mueller-Molaian, I., Marth, T., Zeuzem, S., Meuer, S. C., and Stallmach, A. "Expression of Interleukin-12-related Cytokine Transcripts in Inflammatory Bowel Disease: Elevated lnterleukin-23p19 and Interleukin-27p28 in Crohn's Disease but not in Ulcerative Colitis." *Inflamm. Bowel Dis.* 11:16-23 (2005).

Simone, C., Forcales, S. V., Hill, D. A., Imbalzano, A. N., Latella, L., and Puri, P. L. "p38 Pathway Targets SWI-SNF Chromatin-Remodeling Complex to Muscle-Specific Loci." *Nat. Genet.* 36:738-43 (2004).

Sing, A., A. Roggenkamp, A. M. Geiger, and J. Heesemann. "*Yersinia enterocolitica* Evasion of the Host Innate Immune Response by V Antigen-induced IL-10 Production of Macrophages is Abrogated in IL-10-deficient Mice." *J. Immunol.* 168:1315-21 (2002).

Singer, M., and Sansonetti, P. J. "IL-8 is a Key Chemokine Regulating Neutrbphil Recruitment in a New Mouse Model of *Shigella*-induced Colitis." *J. Immunol.* 173:4197-206 (2004).

Thomson, S., Clayton, A. L., Hazzalin, C. A., Rose, S., Barratt, M. J., and Mahadevan, L. C. "The Nucleosomal Response Associated with Immediate-early Gene Induction is Mediated via Alternative MAP Kinase Cascades: MSK1 as a Potential Histone H3/HMG-14 Kinase." *EMBO J.* 18:4779-93 (1999).

Volmat, V., Camps, M., Arkinstall, S., Pouyssegur, J., and Lenormand, P. "The Nucleus, a Site for Signal Termination by Sequestration, and Inactivation of p42/p44 MAP Kinases." *J. Cell Sci.* 114:3433-43 (2001).

Waetzig, G. H., Seegert, D., Rosenstiel, P., Nikolaus, S., and Schreiber, S. "P38 Mitogen-Activated Protein Kinase is Activated and Linked to TNF-alpha Signaling in Inflammatory Bowel Disease." J. Immunol. 168:5342-51 (2002).

Wang, W., Cho, H. S., Kim, R., Jancarik, J., Yokota, H., Nguyen, H. H., Grigoriev, I. V., Wemmer, D. E., and Kim, S. H. "Structural Characterization of the Reaction Pathway in Phosphoserine Phosphatase: Crystallographic "snapshots" of Intermediate States." *J. Mol. Biol.* 319:421-31 (2002).

Way, S. S., A. C. Borczuk, R. Dominitz, and M. B. Goldberg. "An Essential Role for Gamma Interferon in Innate Resistance to *Shigella flexneri* infection." *Infect. Immun.* 66:1342-48 (1998).

Xia, C., Watton, S., Nagl, S., Samuel, J., Lovegrove, J., Cheshire, J., and Woo, P. "Novel Sites in the p65 Subunit of NF-kappaB Interact with TFIIB to Facilitate NF-kappa B Induced Transcription." *FEBS Lett.* 561:217-22 (2004).

Yan, D., Cho, H. S., Hastings, C. A., Igo, M. M., Lee, S. Y., Pelton, J. G., Stewart, V., Wemmer, D. E., and Kustu, S. "Beryllofluoride Mimics Phosphorylation of NtrC and Other Bacterial Response Regulators." *Proc Natl Acad Sci USA* 96:14789-94 (1999).

Zhang, Z. Y. "Protein Tyrosine Phosphatases: Structure and Function, Substrate Specificity, and Inhibitor Development." *Ann. Rev. Pharmacol. Toxicol.* 42:209-34 (2002).

What is claimed is:

1. A method of determining whether or not a compound modulates OspF activity in a cell, comprising:
   (A) adding a compound to a cultured cell that expresses OspF;
   (B) incubating the cell;
   (C) detecting one or more OspF protein regulation activities in the cell; and
   (D) determining whether or not the compound alters the one or more OspF protein regulation activities in the cell.

2. The method as claimed in claim 1, wherein the protein regulation activity is chosen from regulation of the protein expression and/or activities of activator protein 1 (AP-1), cAMP-response element-binding protein (CREB), replication protein A 32 kiloDalton subunit (RPA p32), antiapoptotic proteins related to B-cell leukemia/lymphoma 2 (BCL2), C-C ligand 20 (CCL20), interleukin 8 (IL-8), or interleukin 12 (IL-12).

3. The method of claim 1, wherein the cell is a HeLa cell, a Caco 2 cell, or a cell of the immune system.

4. The method of claim 1, wherein the cultured cell is a human cell.

5. The method of claim 1, wherein the cultured cell is a cancer cell.

6. The method of claim 5, wherein the cultured cell has been transfected with a plasmid encoding OspF.

7. The method of claim 6, wherein the plasmid encoding OspF is deposited at the CNCM under Accession Number I-3496.

8. The method of claim 1, wherein the cultured cell has been infected with *Shigella flexneri*.

9. The method of claim 1, wherein the protein regulation activity is regulation of the protein expression and/or activities of AP-1.

10. The method of claim 1, wherein the protein regulation activity is regulation of the protein expression and/or activities of CREB.

11. The method of claim 1, wherein the protein regulation activity is regulation of the protein expression and/or activities of RPA p32.

12. The method of claim 1, wherein the protein regulation activity is regulation of the protein expression and/or activities of antiapoptotic proteins related to BCL2.

13. The method of claim 1, wherein the protein regulation activity is regulation of the protein expression and/or activities of CCL20.

14. The method of claim 1, wherein the protein regulation activity is regulation of the protein expression and/or activities of IL-8.

15. The method of claim 1, wherein the protein regulation activity is regulation of the protein expression and/or activities of IL-12.

* * * * *